US011202642B2

(12) United States Patent
Flatt

(10) Patent No.: US 11,202,642 B2
(45) Date of Patent: Dec. 21, 2021

(54) TOOL ASSEMBLY WITH DRIVE SYSTEM COMPRISING COUNTERWEIGHTED CLUTCH

(71) Applicant: MAKO Surgical Corp., Ft. Lauderdale, FL (US)

(72) Inventor: James E. Flatt, Kalamazoo, MI (US)

(73) Assignee: MAKO Surgical Corp., Ft. Lauderdale, FL (US)

( * ) Notice: Subject to any disclaimer, the term of this patent is extended or adjusted under 35 U.S.C. 154(b) by 219 days.

(21) Appl. No.: 16/594,290

(22) Filed: Oct. 7, 2019

(65) Prior Publication Data

US 2020/0030045 A1 Jan. 30, 2020

Related U.S. Application Data

(63) Continuation of application No. 15/789,562, filed on Oct. 20, 2017, now Pat. No. 10,456,207.
(Continued)

(51) Int. Cl.
*A61B 17/16* (2006.01)
*F16D 1/08* (2006.01)
(Continued)

(52) U.S. Cl.
CPC ........ *A61B 17/162* (2013.01); *A61B 17/1624* (2013.01); *A61B 17/1631* (2013.01); *A61B 17/32002* (2013.01); *A61B 34/20* (2016.02); *A61B 34/30* (2016.02); *A61B 34/70* (2016.02); *A61B 90/98* (2016.02); *F16D 1/087* (2013.01); *A61B 17/14* (2013.01); *A61B 17/320068* (2013.01); *A61B 18/082* (2013.01); *A61B 18/148* (2013.01); *A61B 18/18* (2013.01); *A61B 2017/00477* (2013.01);
(Continued)

(58) Field of Classification Search
CPC .............. A61B 17/162; A61B 17/1631; A61B 17/1624; F16D 1/087
See application file for complete search history.

(56) References Cited

U.S. PATENT DOCUMENTS 4,692,073 A 9/1987 Martindell
5,013,194 A 5/1991 Wienhold
(Continued)

FOREIGN PATENT DOCUMENTS

EP 2272446 A2 1/2011

OTHER PUBLICATIONS

International Search Report for Application No. PCT/US2017/057673 dated Mar. 26, 2018, 3 pages.
(Continued)

*Primary Examiner* — Christian A Sevilla
(74) *Attorney, Agent, or Firm* — Howard & Howard Attorneys PLLC

(57) ABSTRACT

Disclosed herein is a tool assembly for use with an energy applicator having a shaft extending along an axis between a proximal end and a distal end. The tool assembly comprises a support structure to support the energy applicator, and a connector assembly arranged to engage and releasably lock the energy applicator to the support structure in a locked state. A drive system is coupled to the support structure and is configured to rotatably drive the shaft of the energy applicator about the axis. The drive system comprises a counterweighted clutch assembly.

18 Claims, 23 Drawing Sheets

Related U.S. Application Data

(60) Provisional application No. 62/411,039, filed on Oct. 21, 2016.

(51) Int. Cl.

| | | |
|---|---|---|
| *A61B 90/98* | (2016.01) |
| *A61B 17/32* | (2006.01) |
| *A61B 34/00* | (2016.01) |
| *A61B 34/20* | (2016.01) |
| *A61B 34/30* | (2016.01) |
| *A61B 18/00* | (2006.01) |
| *A61B 17/14* | (2006.01) |
| *A61B 18/08* | (2006.01) |
| *A61B 18/14* | (2006.01) |
| *A61B 18/18* | (2006.01) |
| *A61B 17/00* | (2006.01) |

(52) U.S. Cl.
CPC ............ *A61B 2018/00172* (2013.01); *A61B 2018/00208* (2013.01); *A61B 2018/00565* (2013.01); *A61B 2018/00601* (2013.01); *A61B 2018/1807* (2013.01); *A61B 2034/2055* (2016.02); *A61B 2034/2057* (2016.02); *A61B 2034/2059* (2016.02); *A61B 2034/2068* (2016.02)

(56) References Cited

U.S. PATENT DOCUMENTS

| | | | |
|---|---|---|---|
| 5,595,273 A * | 1/1997 | Endoy | F16D 41/064 |
| | | | 192/103 B |
| 9,008,757 B2 | 4/2015 | Wu | |
| 9,119,655 B2 | 9/2015 | Bowling et al. | |
| 10,456,207 B2 | 10/2019 | Flatt | |
| 2005/0277869 A1* | 12/2005 | Boukhny | A61F 9/00745 |
| | | | 604/22 |
| 2008/0167652 A1* | 7/2008 | Reinhard | B23B 51/0473 |
| | | | 606/80 |
| 2011/0243673 A1* | 10/2011 | Svagr | B23B 47/00 |
| | | | 408/1 R |
| 2012/0330429 A1 | 12/2012 | Axelson, Jr. et al. | |
| 2014/0276949 A1 | 9/2014 | Staunton et al. | |
| 2018/0168639 A1* | 6/2018 | Shelton, IV | A61B 17/29 |

OTHER PUBLICATIONS

Partial International Search Report for PCT/US2017/057673 dated Jan. 26, 2018, 3 pages.

\* cited by examiner

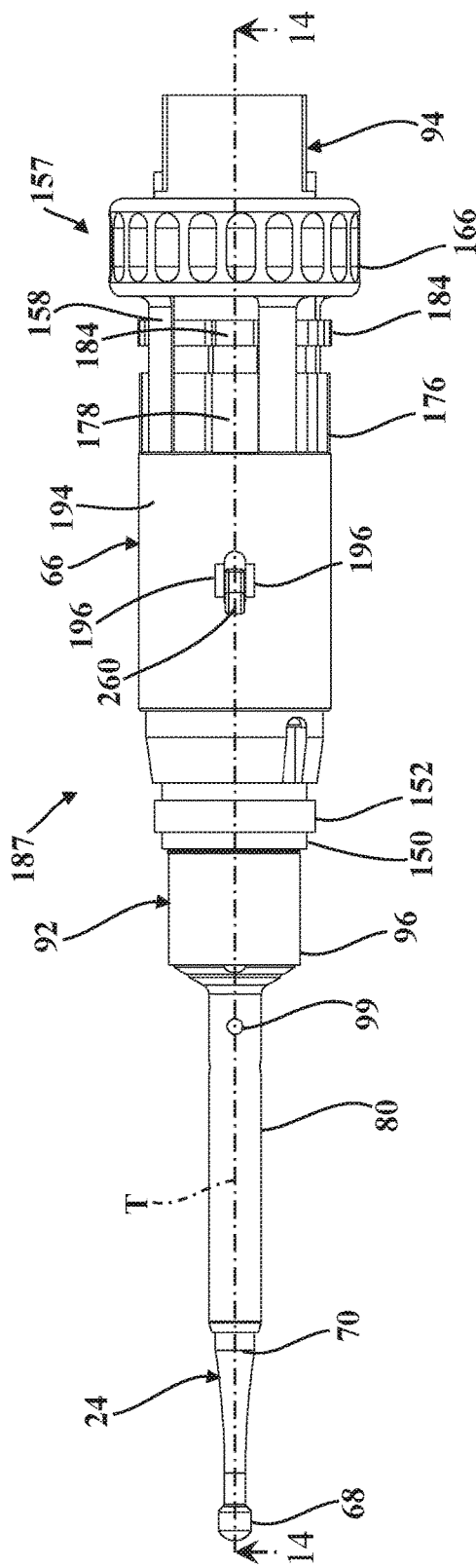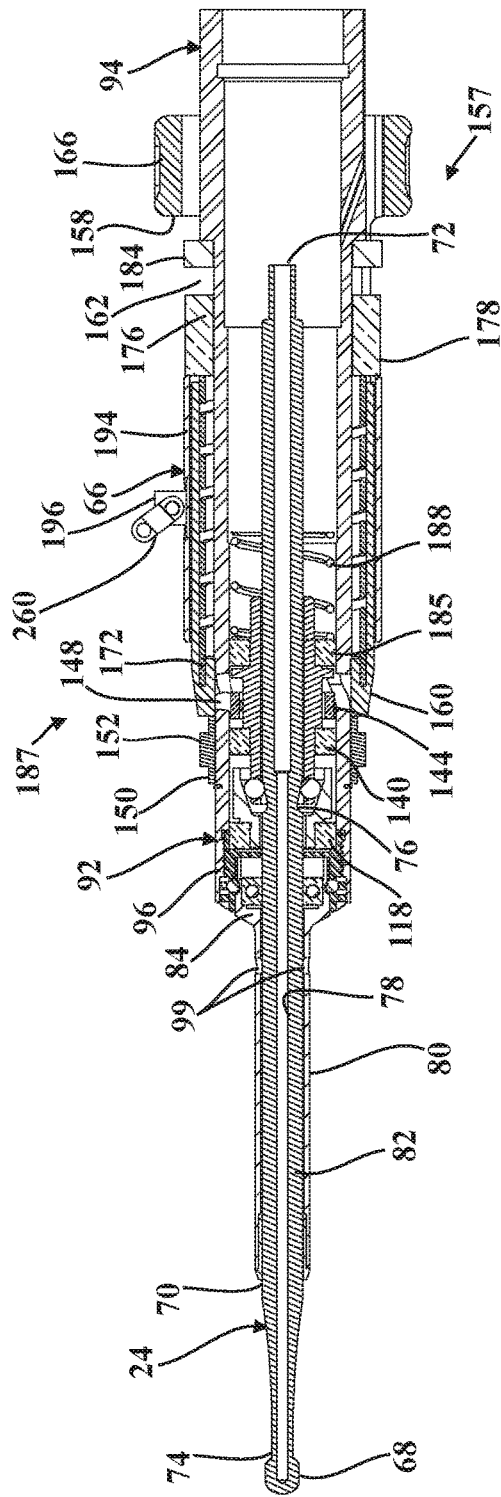
FIG. 13
FIG. 14

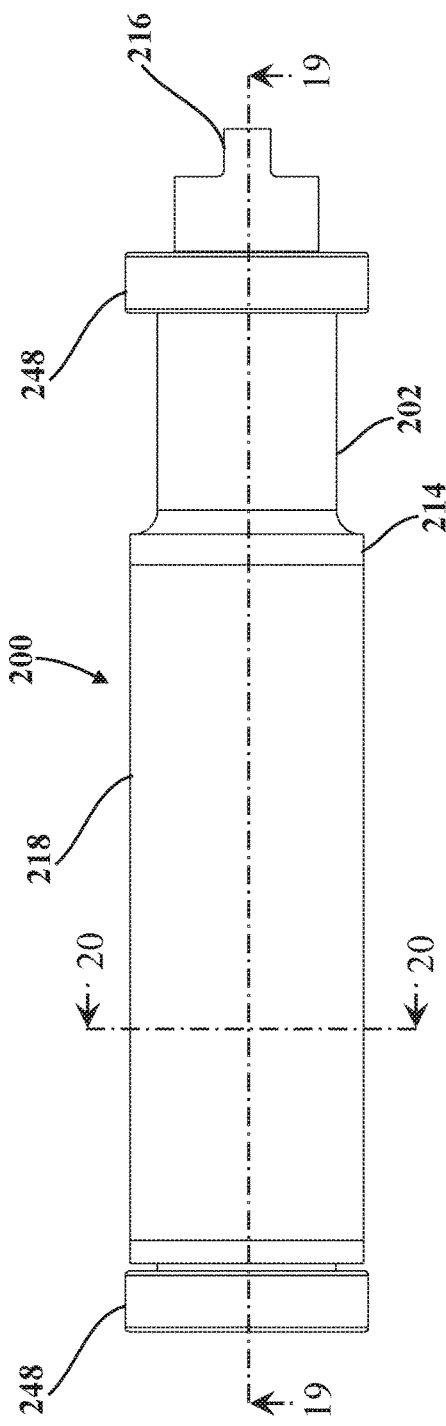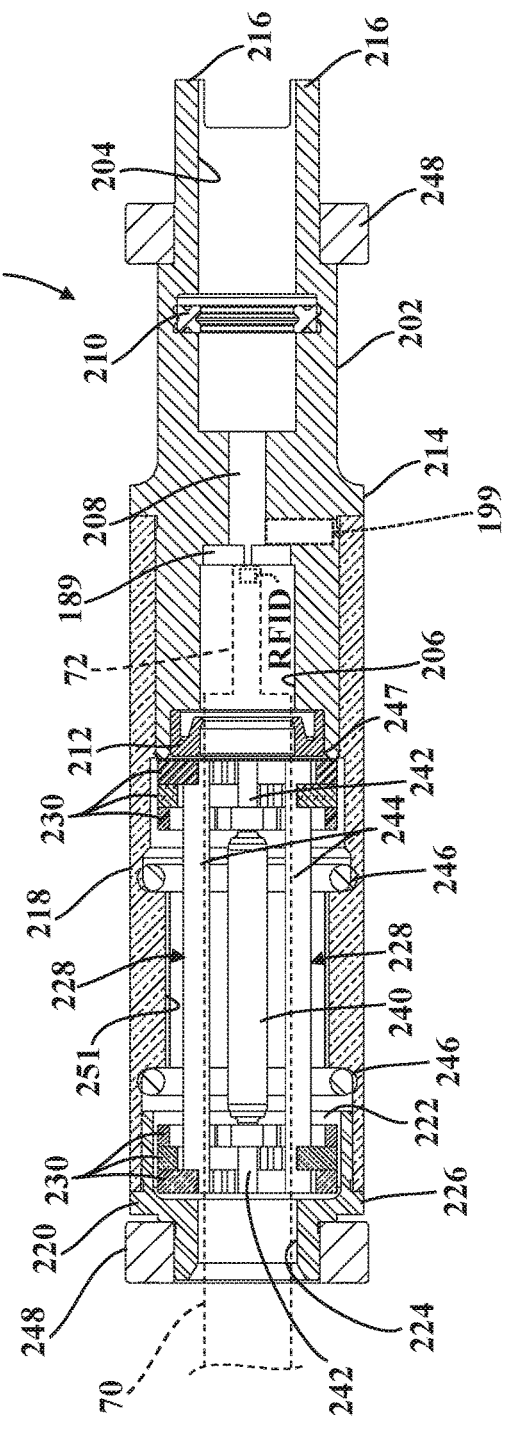

TOOL ASSEMBLY WITH DRIVE SYSTEM COMPRISING COUNTERWEIGHTED CLUTCH

CROSS-REFERENCE TO RELATED APPLICATIONS

This application is a continuation of U.S. patent application Ser. No. 15/789,562, filed Oct. 20, 2017, which claims priority to and all the benefits of U.S. Provisional Patent Application No. 62/411,039 which was filed on Oct. 21, 2016, the disclosures of each of which are hereby incorporated by reference in their entirety.

TECHNICAL FIELD

The present disclosure relates, generally, to surgical tools and, more particularly, to systems and tools for use with surgical robotic manipulators.

BACKGROUND

Medical practitioners have found it useful to use surgical robotic manipulators to assist in the performance of surgical procedures. An example of an end effector for a surgical robotic manipulator is disclosed in U.S. Patent Application Publication No. 2014/0276949. There is a need in the art to continuously improve such end effectors.

SUMMARY

One example of a tool is provided. The tool comprises an energy applicator including a shaft extending along an axis between a proximal end and a distal end; and a tool assembly comprising a support structure to support the energy applicator, a connector assembly arranged to engage and releasably lock the energy applicator to the support structure in a locked state, and a drive system coupled to the support structure and configured to rotatably drive the shaft of the energy applicator about the axis; wherein the drive system comprises a counterweighted clutch assembly.

One example of a tool assembly is provided. The tool assembly is for use with an energy applicator having a shaft extending along an axis between a proximal end and a distal end, the tool assembly comprising: a support structure to support the energy applicator; a connector assembly arranged to engage and releasably lock the energy applicator to the support structure in a locked state; and a drive system coupled to the support structure and configured to rotatably drive the shaft of the energy applicator about the axis; wherein the drive system comprises a counterweighted clutch assembly.

Other features and advantages of the present disclosure will be readily appreciated, as the same becomes better understood, after reading the subsequent description taken in conjunction with the accompanying drawings.

BRIEF DESCRIPTION OF THE DRAWINGS

FIG. 13 is an elevational view of the energy applicator, protective sheath, and the tool assembly of FIG. 11.

FIG. 14 is a cross-sectional view taken along line 14-14 of FIG. 13.

FIG. 18 is an elevational view of the drive assembly of FIG. 16.

FIG. 19 is a cross-sectional view taken along line 19-19 of FIG. 18.

Certain of the Figures set forth above may have portions of the end effector removed for purposes of illustration.

DETAILED DESCRIPTION

Figure 1:
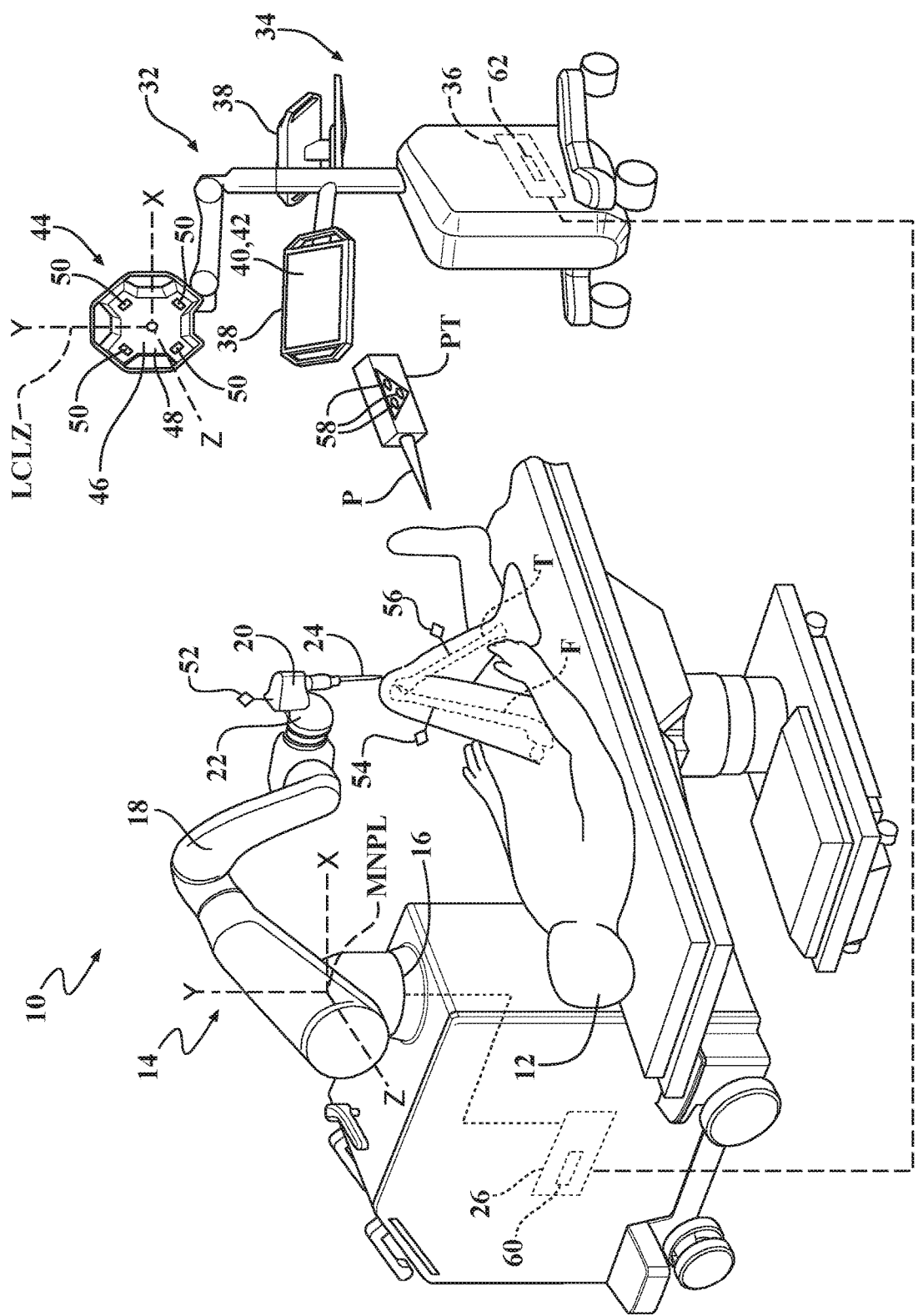
FIG. 1 is a perspective view of a surgical robotic system including a surgical robotic manipulator and an end effector performing a surgical procedure on a patient.

Referring now to the Figures, wherein like numerals indicate like or corresponding parts throughout the several views, a system 10 for manipulating an anatomy of a patient 12 are shown throughout. As shown in FIG. 1, the system 10 is a robotic surgical cutting system for cutting away material from the anatomy of the patient 12, such as bone or soft tissue. In FIG. 1, the patient 12 is undergoing a surgical procedure, and the anatomy includes a femur (F) and a tibia (T) of the patient 12. The surgical procedure may involve tissue removal. In some embodiments, the surgical procedure involves partial or total knee or hip replacement surgery. The system 10 is designed to cut away material to be replaced by surgical implants such as hip and knee implants, including unicompartmental, bicompartmental, total knee implants, and other types of prosthetics. Some of these types of implants are disclosed in U.S. Patent Application Publication No. 2012/0330429, entitled, "Prosthetic Implant and Method of Implantation," the entire disclosure of which is hereby expressly incorporated by reference. It should be appreciated that the system 10 disclosed herein may be used to perform other procedures, either surgical or non-surgical, and/or may be used in industrial applications or other applications.

The system 10 includes a surgical manipulator 14 (e.g., a surgical robot). The manipulator 14 has a base 16 and a linkage 18 (e.g., an articulable robotic arm). The linkage 18 may include links forming a serial arm or parallel arm configuration. A tool 20 couples to the manipulator 14 and is movable relative to the base 16 via the linkage 18 to interact with the anatomy of the patient 12. The tool 20 forms part of an end effector 22 attached to the manipulator 14. The tool 20 is grasped by the operator (e.g., a surgeon) in some embodiments. One exemplary arrangement of the manipulator 14 and the tool 20 is described in U.S. Pat. No. 9,119,655, entitled, "Surgical Manipulator Capable of Controlling a Surgical Instrument in Multiple Modes," the entire disclosure of which is hereby expressly incorporated by reference. The manipulator 14 and the tool 20 may be arranged in alternative configurations. The tool 20 comprises an energy applicator 24 to contact the tissue of the patient 12 at a surgical site. The energy applicator 24 may be a drill, a saw blade, a bur, an ultrasonic vibrating tip, or the like. Other configurations are contemplated. The manipulator 14 houses a manipulator computer 26, or other type of control unit.

The system 10 includes a controller which includes software and/or hardware for controlling the manipulator 14. The controller directs the motion of the manipulator 14 and controls a position and orientation of the tool 20 with respect to a coordinate system. In one embodiment, the coordinate system is a manipulator coordinate system MNPL (see FIG. 1). The manipulator coordinate system MNPL has an origin, and the origin is located relative to the manipulator 14. One example of the manipulator coordinate system MNPL is described in U.S. Pat. No. 9,119,655, entitled, "Surgical Manipulator Capable of Controlling a Surgical Instrument in Multiple Modes," previously referenced.

The system 10 further includes a navigation system 32. One example of the navigation system 32 is described in U.S. Pat. No. 9,008,757, filed on Sep. 24, 2013, entitled, "Navigation System Including Optical and Non-Optical Sensors," the entire disclosure of which is hereby expressly incorporated by reference. The navigation system 32 is set up to track movement of various objects. Such objects include, for example, the tool 20, and the anatomy, e.g., femur F and tibia T. The navigation system 32 tracks these objects to gather position information of each object in a localizer coordinate system LCLZ. Coordinates in the localizer coordinate system LCLZ may be transformed to the manipulator coordinate system MNPL using conventional transformation techniques. In some embodiments, the navigation system 32 is also capable of displaying a virtual representation of their relative positions and orientations to the operator.

The navigation system 32 includes a computer cart assembly 34 that houses a navigation computer 36, and/or other types of control units. A navigation interface is in operative communication with the navigation computer 36. The navigation interface includes one or more displays 38. First and second input devices 40, 42 such as touch screen inputs may be used to input information into the navigation computer 36 or otherwise select/control certain aspects of the navigation computer 36. Other input devices are contemplated, including a keyboard, mouse, voice-activation, and the like. The controller may be implemented on any suitable device or devices in the system 10, including, but not limited to, the manipulator computer 26, the navigation computer 36, and any combination thereof.

The navigation system 32 also includes a localizer 44 that communicates with the navigation computer 36. In one embodiment, the localizer 44 is an optical localizer and includes a camera unit 46. The camera unit 46 has an outer casing 48 that houses one or more optical position sensors 50. The system 10 also includes one or more trackers. The trackers may include a pointer tracker PT, a tool tracker 52, a first patient tracker 54, and a second patient tracker 56. The trackers include active markers 58. The active markers 58 may be light emitting diodes or LEDs. In other embodiments, the trackers 52, 54, 56 may have passive markers, such as reflectors, which reflect light emitted from the camera unit 46. It should be appreciated that other suitable tracking systems and methods not specifically described herein may be utilized.

In the illustrated embodiment of FIG. 1, the first patient tracker 54 is firmly affixed to the femur F of the patient 12 and the second patient tracker 56 is firmly affixed to the tibia T of the patient 12. The patient trackers 54, 56 are firmly affixed to sections of bone. The tool tracker 52 is firmly attached to the tool 20. It should be appreciated that the trackers 52, 54, 56 may be fixed to their respective components in any suitable manner.

The trackers 52, 54, 56 communicate with the camera unit 46 to provide position data to the camera unit 46. The camera unit 46 provides the position data of the trackers 52, 54, 56 to the navigation computer 36. In one embodiment, the navigation computer 36 determines and communicates position data of the femur F and tibia T and position data of the tool 20 to the manipulator computer 26. Position data for the femur F, tibia T, and tool 20 may be determined by the tracker position data using conventional registration/navigation techniques. The position data include position information corresponding to the position and/or orientation of the femur F, tibia T, tool 20, and/or any other objects being tracked. The position data described herein may be position data, orientation data, or a combination of position data and orientation data.

The manipulator computer 26 transforms the position data from the localizer coordinate system LCLZ into the manipulator coordinate system MNPL by determining a transformation matrix using the navigation-based data for the tool 20 and encoder-based position data for the tool 20. Encoders (not shown) located at joints of the manipulator 14 are used to determine the encoder-based position data. The manipulator computer 26 uses the encoders to calculate an encoder-based position and orientation of the tool 20 in the manipulator coordinate system MNPL. Since the position and orientation of the tool 20 are also known in the localizer coordinate system LCLZ, the transformation matrix may be generated.

In one embodiment, the controller includes a manipulator controller 60 for processing data to direct motion of the manipulator 14. The manipulator controller 60 may receive and process data from a single source or from multiple sources.

The controller further includes a navigation controller 62 for communicating the position data relating to the femur F, tibia T, and tool 20 to the manipulator controller 60. The manipulator controller 60 receives and processes the position data provided by the navigation controller 62 to direct movement of the manipulator 14. In one embodiment, as shown in FIG. 1, the navigation controller 62 is implemented on the navigation computer 36.

The manipulator controller 60 or navigation controller 62 may also communicate positions of the patient 12 and the tool 20 to the operator by displaying an image of the femur F and/or tibia T and the tool 20 on the display 38. The manipulator computer 26 or navigation computer 36 may also display instructions or request information on the display 38 such that the operator may interact with the manipulator computer 26 for directing the manipulator 14. Other configurations are contemplated.

Figure 2:
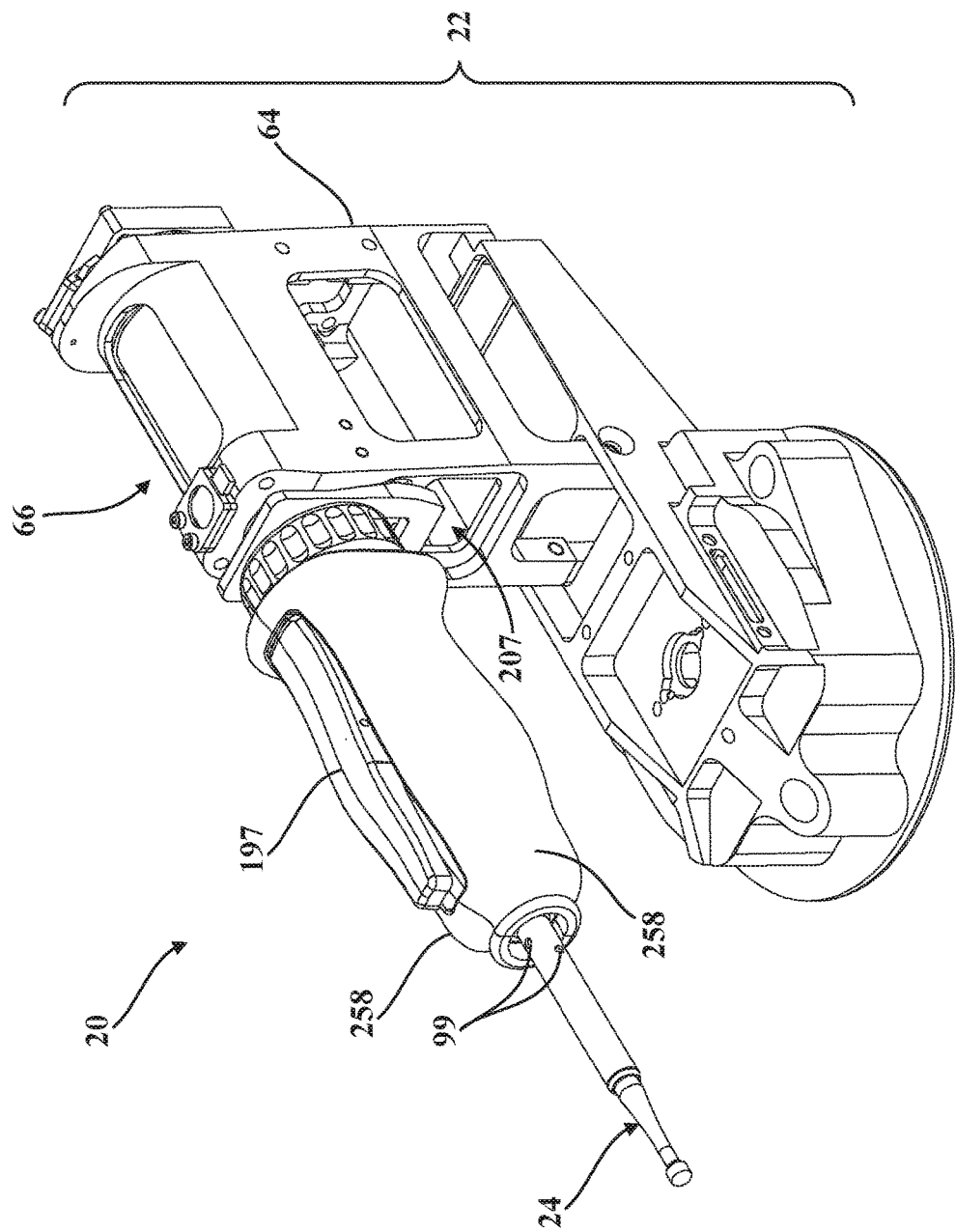
FIG. 2 is a perspective view of one embodiment of the end effector comprising a surgical tool.

Referring to FIG. 2, in some embodiments, the tool 20 includes a drive system 66 that converts electrical signals into a form of energy that is applied to the patient. This energy may be mechanical, ultrasonic, thermal, RF, EM, photonic, combinations thereof, and the like. The energy is applied to the patient 12 through the energy applicator 24. In the representative embodiment shown, the end effector 22 includes a mounting fixture 64 for removably attaching the tool 20 to the manipulator 14. In the embodiment shown, the energy applicator 24 is configured to remove tissue of the patient. As shown in the Figures, the energy applicator 24 comprises a bur. Alternative to a bur, the energy applicator 24 may comprise any type of surgical tool for material cutting, material removal, or other tissue manipulation or treatment at a surgical site.

Figure 3:
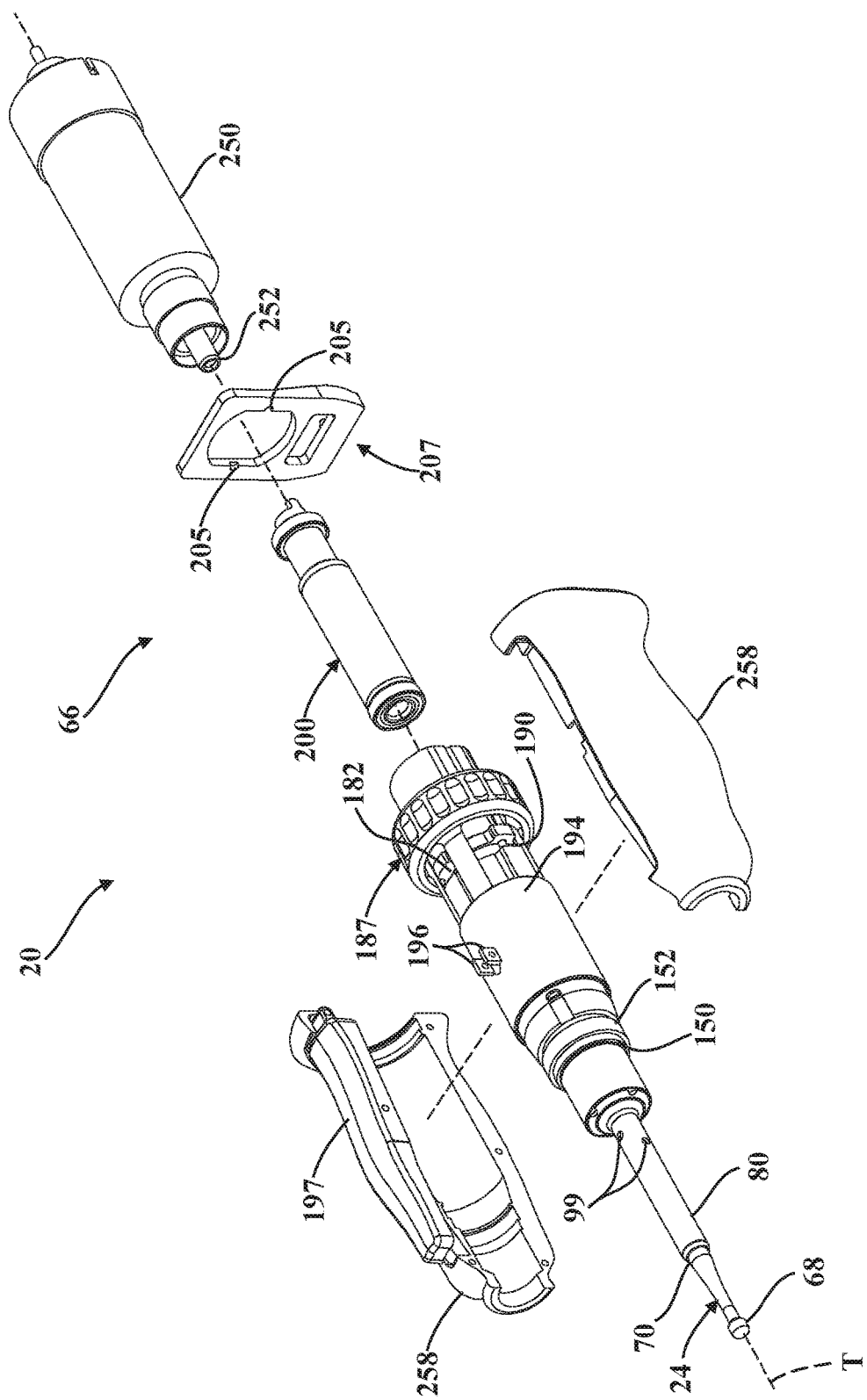
FIG. 3 is an exploded view of the surgical tool.
Figure 4:
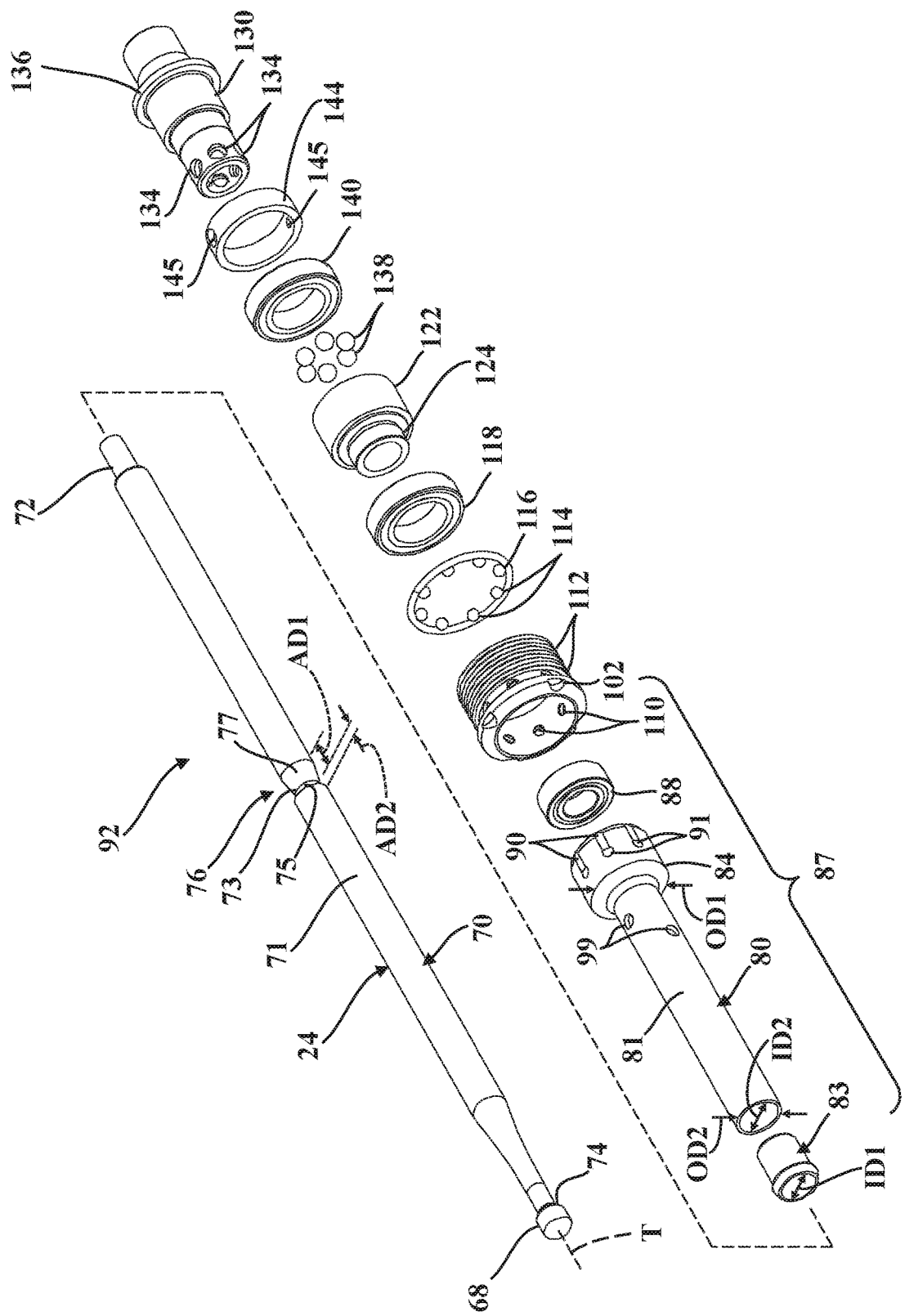
FIG. 4 is an exploded view of an energy applicator, a protective sheath, and an axial connector assembly.
Figure 5:
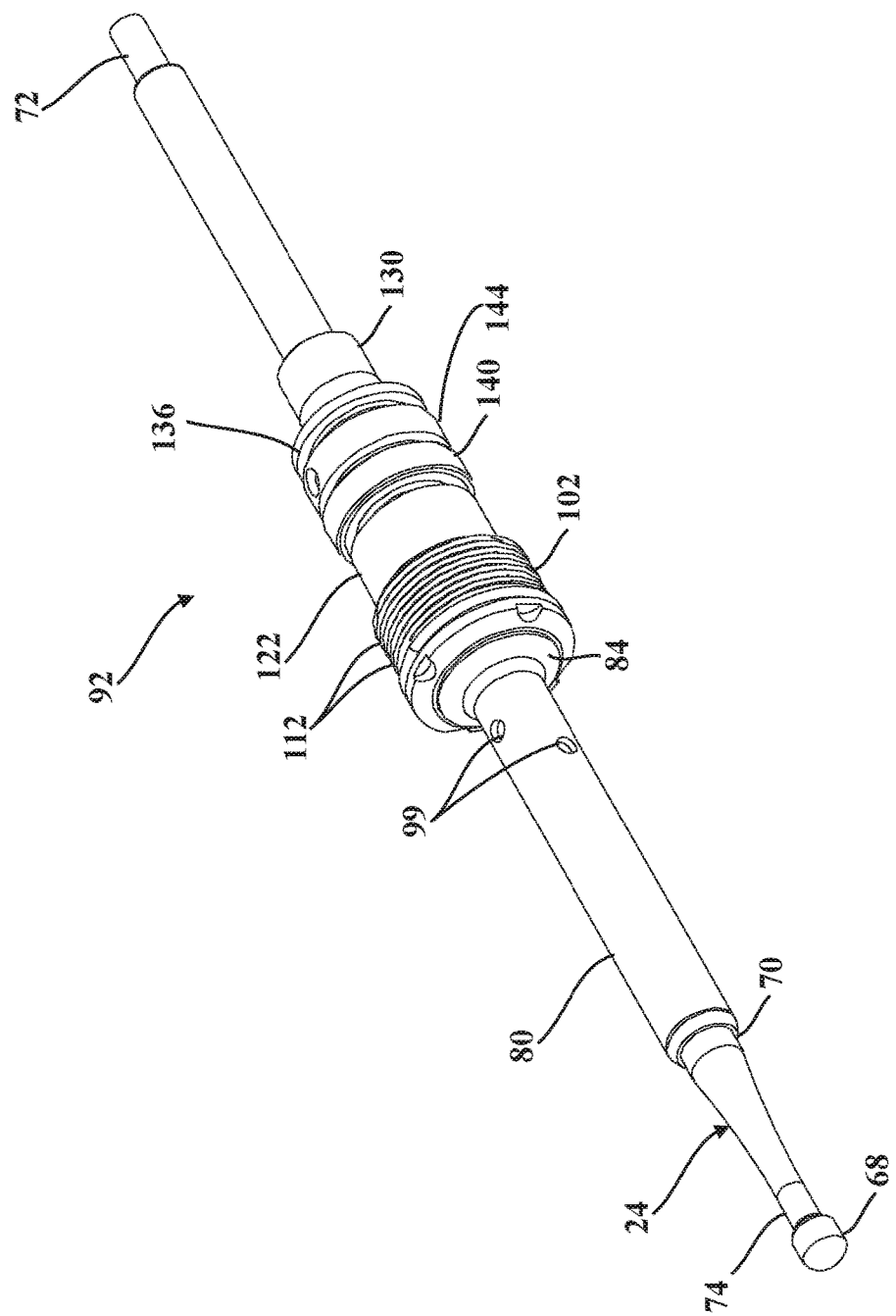
FIG. 5 is a perspective view of the energy applicator, protective sheath, and axial connector assembly of FIG. 4.

With reference to FIGS. 3 and 4, in the embodiment shown, the energy applicator 24 includes a working portion comprising a head 68 for cutting tissue of the patient 12, and a shaft 70 extending along a tool axis T between a proximal end 72 and a distal end 74. The shaft 70 includes an outer surface 71 in which an annular groove or recess 76 is disposed. The groove or recess 76 is arranged axially between the proximal end 72 and the distal end 74, and extends radially inward toward the tool axis T to a bottom 73. Put differently, the groove or annular recess 76 depends inwardly from the outer surface 71 to the bottom 73. As is explained in greater detail below, the groove or annular recess 76 at least partially defines an axial-force receiving surface to promote axial retention of the energy applicator 24.

The groove or annular recess 76 has a distal surface 75 and a sloped surface 77, each of which extends from the outer surface 71 of the shaft 70 to the bottom 73. In the illustrated embodiment, the distal surface 75 has a generally toroidal profile and is arranged axially between the distal end 74 and the bottom 73, and the sloped surface 77 has a generally conical profile and is arranged axially between the bottom 73 and the proximal end 72. As shown in FIG. 4, the conical, sloped surface 77 is formed extending along a first axial distance AD1 from the outer surface 71 to the bottom 73, and the distal surface 75 is formed extending along a second axial distance AD2, less than the first axial distance AD1, from the outer surface 71 to the bottom 73. It will be appreciated that the annular groove or recess 76 could have different configurations sufficient to promote axial retention of the energy applicator 24.

Figure 9:
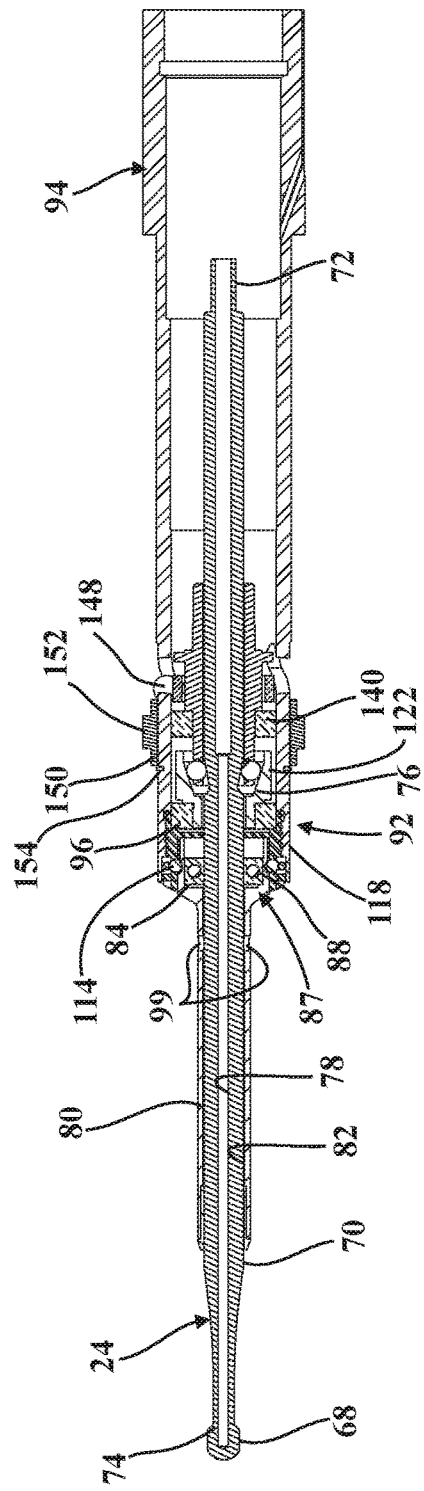
FIG. 9 is a cross-sectional view taken along line 9-9 of FIG. 8.
Figure 10:
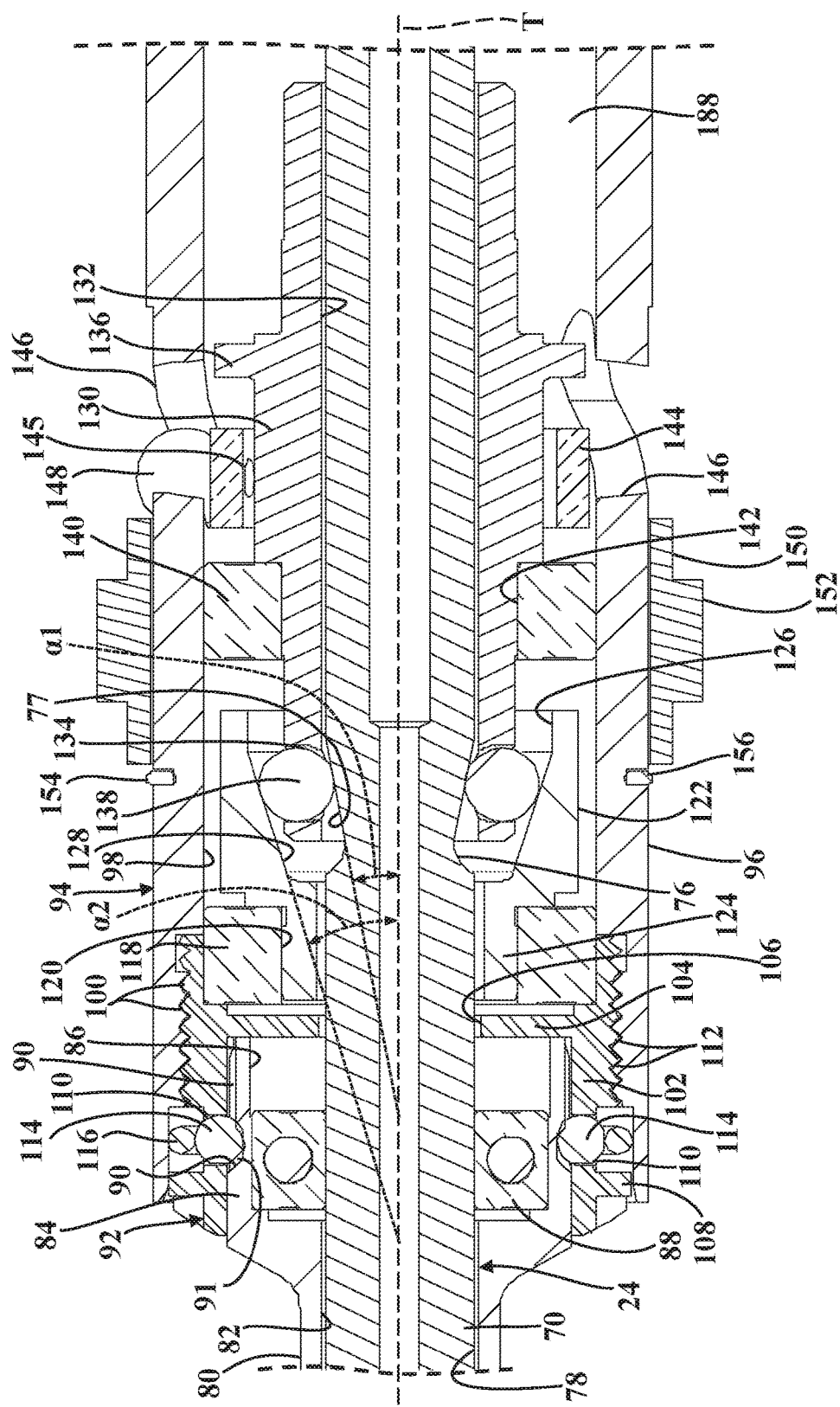
FIG. 10 is an enlarged view of a portion of FIG. 9.
Figure 11:
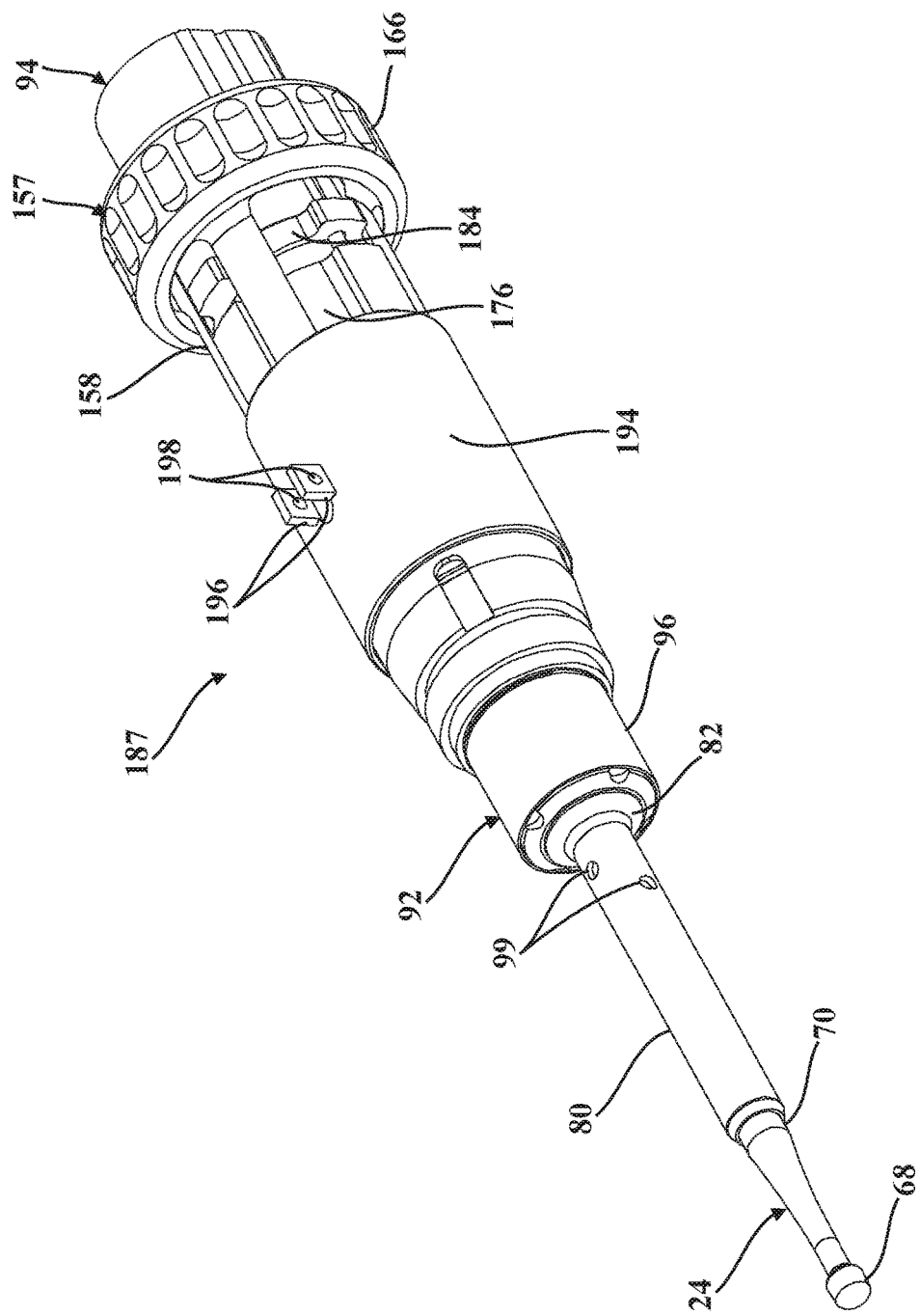
FIG. 11 is a perspective view of the energy applicator, protective sheath, and a tool assembly, the tool assembly comprising the axial connector assembly, the support structure, and a collet assembly.
Figure 12:
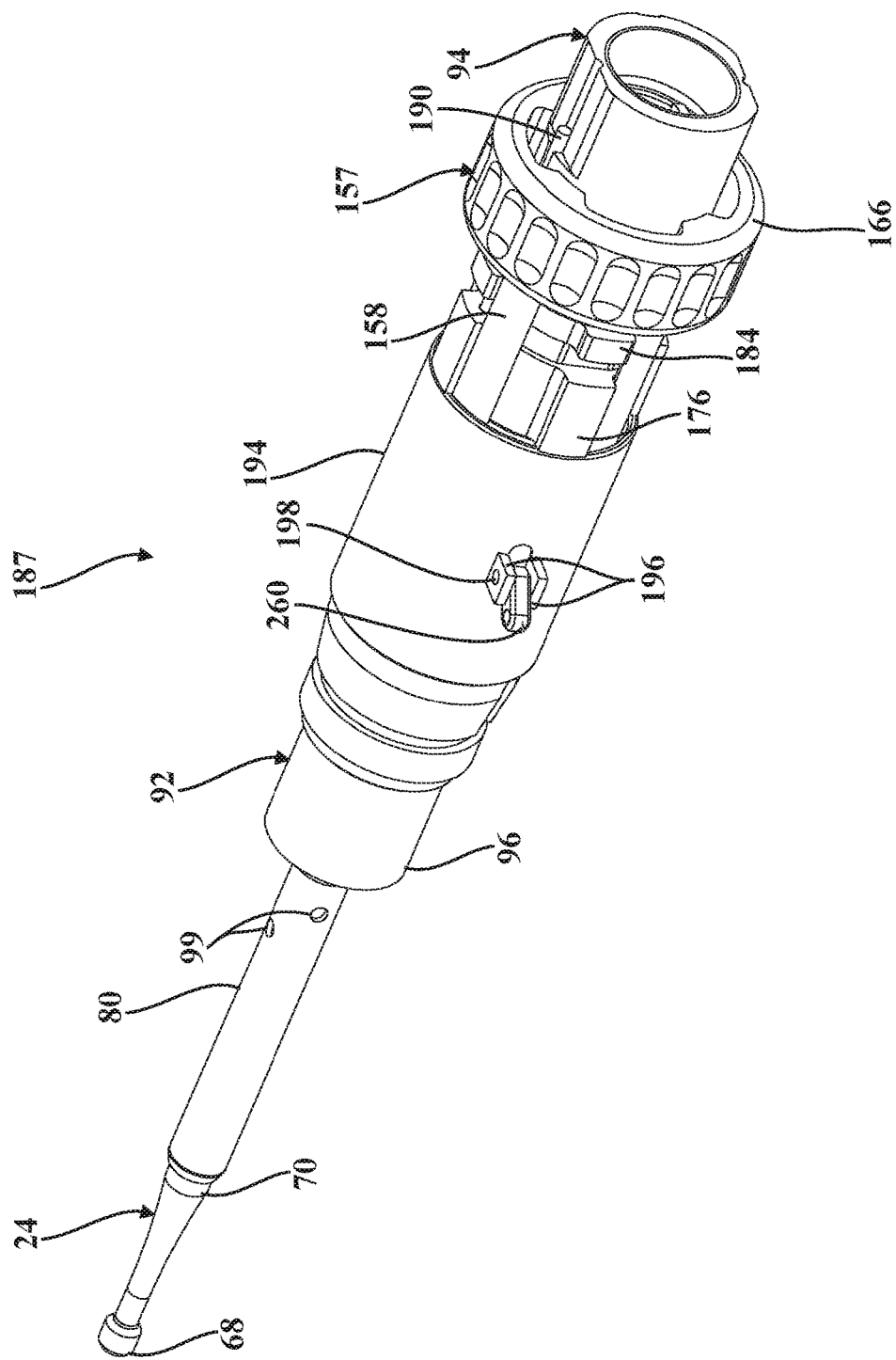
FIG. 12 is another perspective view of the energy applicator, protective sheath, and the tool assembly of FIG. 11.

The conical, sloped surface 77 is arranged at an acute angle $\alpha_1$ relative to the axis T (see FIG. 10). In some embodiments, the acute angle $\alpha_1$ is greater than zero degrees and less than 90 degrees. In other embodiments, the acute angle $\alpha_1$ is 5-60 degrees, 10-30 degrees, or 10-20 degrees, relative to the axis T. The shaft 70 may include a passage 78 (see FIG. 9) extending axially between the proximal end 72 and the distal end 74 for purposes of irrigation and/or suction. In the embodiment shown, the head 68 and shaft 70 of the energy applicator 24 are integral, unitary, and one-piece, but could be separate parts in other embodiments.

Referring to FIG. 4 through 10, a protective sheath 80 supports the energy applicator 24. The protective sheath 80 comprises a nose tube 81 and defines a protective sheath bore 82 (see FIG. 9) and receives the shaft 70 of the energy applicator 24 in the protective sheath bore 82. The protective sheath 80 includes an enlarged end portion 84 which is configured for releasable attachment, as is described in greater detail below. The nose tube 81 is formed integrally with and extends from the end portion 84, and a distal bushing 83 is attached to the distal end of the nose tube 81. The distal bushing 83 is configured to be concentrically disposed about the shaft 70 of the energy applicator 24. As is depicted in FIG. 4, the distal bushing 83 has a first inner diameter ID1, and the nose tube 81 has a second inner diameter ID2 which is larger than the first inner diameter ID2. Here too in FIG. 4, the end portion 84 has a first outer diameter OD1 and the nose tube 81 has a second outer diameter OD2 which is smaller than the first outer diameter OD2.

The enlarged end portion 84 has a cavity 86 and at least one bearing 88, shown for example in FIG. 10, disposed in the cavity 86. In some embodiments, the protective sheath 80 and the bearing 88 form a releasably attachable protective sheath assembly 87 (see FIG. 4). The bearing 88 is configured to receive and rotatably support the shaft 70 in the protective sheath bore 82. The enlarged end portion 84 has one or more outer grooves 90 extending axially. The grooves 90 are circumferentially and equally spaced about an outer periphery of the enlarged end portion 84. The grooves 90 are spaced circumferentially about the outer surface and extend from a proximal end of the enlarged end portion 84 to a detent pocket 91. In the illustrated embodiments, the grooves 90 are shallower than their corresponding detent pockets 91, and extend axially from the respective detent pockets 91 to the proximal end of the end portion 84 of the protective sheath 80. However, it will be appreciated that other configurations are contemplated.

Figure 6:
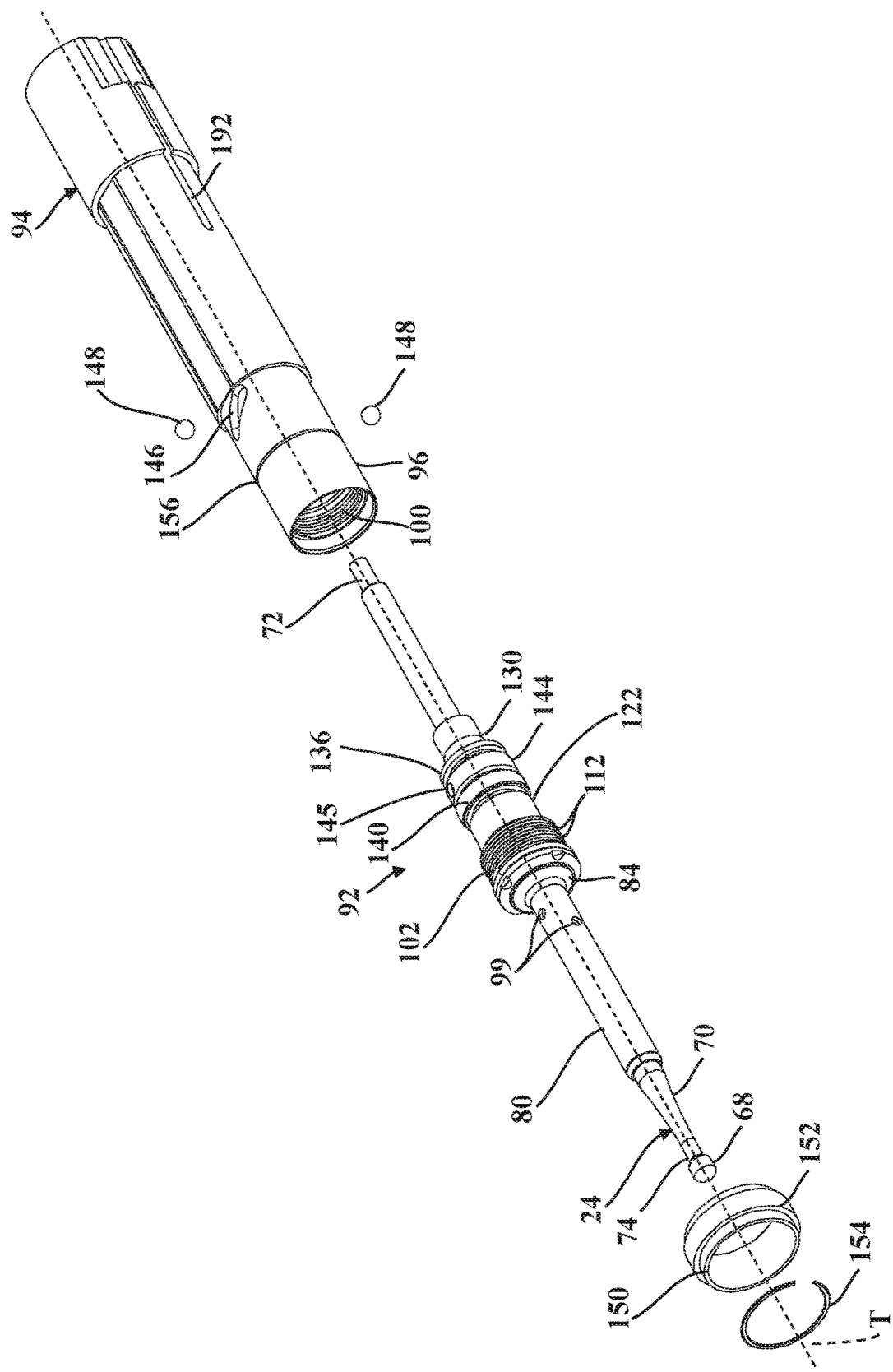
FIG. 6 is an exploded view of the energy applicator, protective sheath, and axial connector assembly of FIG. 4 already pre-assembled and a support structure.
Figure 7:
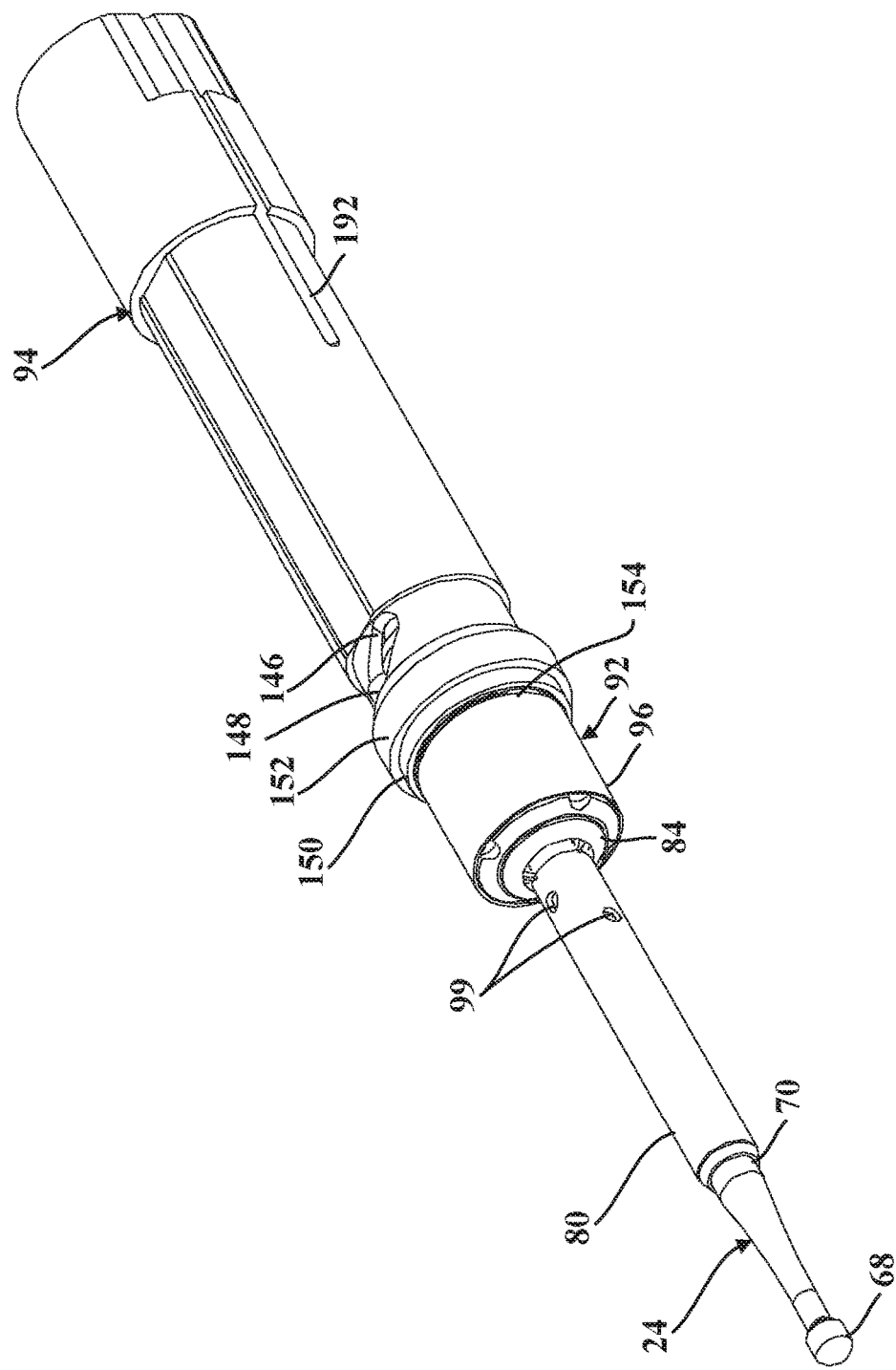
FIG. 7 is a perspective view of the energy applicator, protective sheath, axial connector assembly, and the support structure of FIG. 6.
Figure 8:
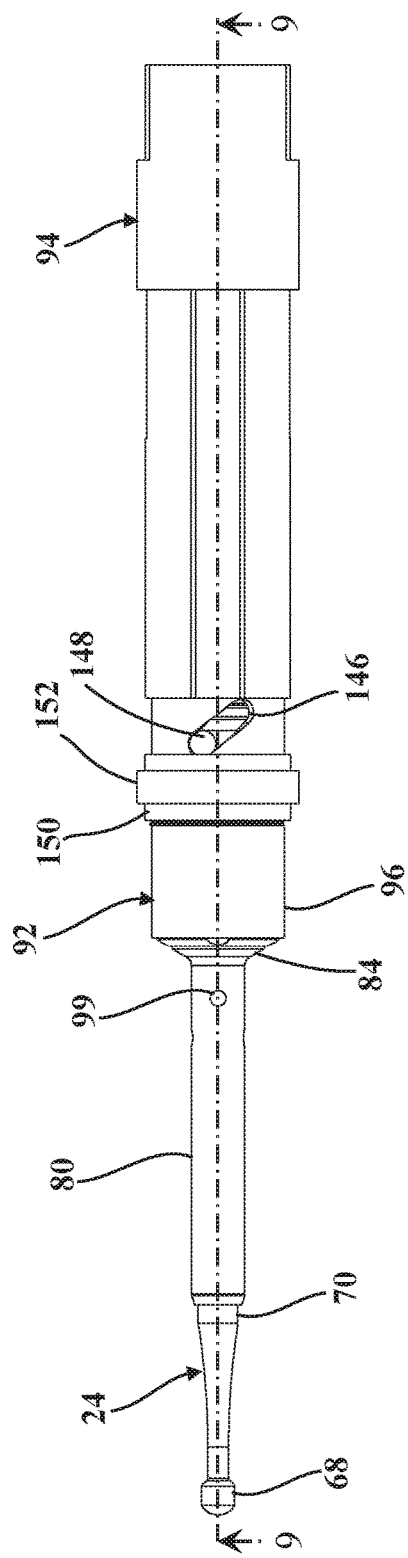
FIG. 8 is an elevational view of the energy applicator, protective sheath, axial connector assembly, and the support structure of FIG. 6.

An axial connector assembly 92 couples the energy applicator 24 and the protective sheath 80 to a support structure 94 (see FIG. 6). As set forth further below, the connector assembly 92 supports the protective sheath 80 and is configured to support or lock the energy applicator 24 relative to the protective sheath 80. The axial connector assembly 92 and the support structure 94 are concentrically disposed relative to each other along the axis T. The axial connector assembly 92 releasably engages the energy applicator 24 and the protective sheath 80 such that both of the energy applicator 24 and the protective sheath 80 are replaceable components.

Referring to FIG. 10, in the illustrated embodiment, the support structure 94 includes a support sleeve 96 extending axially. The support sleeve 96 is generally cylindrical in shape. The support sleeve 96 has a hollow interior cavity 98 with a plurality of internal threads 100 at a distal end thereof. The axial connector assembly 92 includes a connector member 102 to facilitate releasable connection of the protective sheath 80 to the support sleeve 96. The connector member 102 includes a plurality of exterior threads 112 to threadably engage the interior threads 100 of the support sleeve 96. The connector member 102 is generally cylindrical in shape.

The connector member 102 includes an interior wall 104 extending radially inwardly to act as a stop for the enlarged end portion 84 of the protective sheath 80 when inserting the protective sheath 80 into the connector member 102. The interior wall 104 has an aperture 106 extending axially therethrough to allow the shaft 70 of the energy applicator 24 to extend therethrough. The connector member 102 includes a flange 108 extending radially outward to engage an interior surface of the support sleeve 96.

The connector member 102 also includes one or more openings 110 (see also FIG. 4) extending radially therethrough. The openings 110 are disposed axially between the interior wall 104 and the flange 108. In the embodiment shown, the connector member 102 is integral, unitary, and one-piece, but could be separate parts in other embodiments.

The axial connector assembly 92 also includes at least one engagement member 114 to releasably couple the protective sheath 80 to the connector member 102. In one embodiment, a plurality of engagement members 114 are used with one engagement member 114 disposed in each opening 110. Each of the engagement members 114 is generally spherical in shape. In the embodiment shown, the engagement members 114 are ball bearings, such as those formed of stainless steel or other suitable materials. The axial connector assembly 92 can include any number of engagement members 114 and corresponding openings 110.

The axial connector assembly 92 also includes a resilient member 116 disposed about the engagement members 114. The resilient member 116 may be an O-ring seal, but may have other forms, such as a compression spring or other type of spring. The resilient member 116 presses the engagement members 114 into their corresponding openings 110 to facilitate a releasable connection to the enlarged end portion 84 of the protective sheath 80.

Each of the openings 110 are sized and shaped so that the engagement members 114 are capable of being exposed on either side of the openings 110. By being exposed on a radially outward side of the openings 110, the resilient member 116 can apply a biasing force to the engagement members 114. By being exposed on a radially inward side of the openings 110, the engagement members 114 are able to engage the enlarged end portion 84 of the protective sheath 80. The openings 110 may be sized and shaped to receive the engagement members 114 without allowing the engagement members 114 to fall through the openings 110 when the protective sheath 80 is absent. For instance, the openings 110 could be tapered radially inwardly to a diameter sized to retain the engagement members 114.

When axially coupling the protective sheath 80 to the connector member 102 (which is already fixed to the support sleeve 96), the engagement members 114 are sized and shaped to move along and within the grooves 90 defined in the enlarged end portion 84, under constant bias of the resilient member 116 until the engagement members 114 reach (e.g., are radially aligned with) the detent pockets 91. At that point, the engagement members 114 are seated in the detent pockets 91 thereby holding the protective sheath 80 to the connector member 102 by virtue of the bias associated with the resilient member 116. The protective sheath 80 may be removed by pulling on the protective sheath 80 distally to overcome the bias and urge the engagement members 114 out from the detent pockets 91.

The protective sheath 80 may require replacement when the bearing 88 is worn. Accordingly, by having the bearing 88 supported in the protective sheath 80 and making the protective sheath 80 removable and replaceable, significant down time can be avoided that might otherwise exist if the entire end effector 22 needed to be taken out of circulation to replace the bearing 88.

The protective sheath 80 defines one or more weep holes 99 extending radially therethrough. The weep holes 99 may be spaced axially and/or circumferentially about the protective sheath 80. In the embodiment shown, a first pair of diametrically opposing weep holes 99 are located near the enlarged end portion 84 of the protective sheath 80 at a first axial distance from the enlarged end portion 84. A second pair of diametrically opposing weep holes 99 are located further away from the enlarged end portion 84 at a second axial distance. The second pair of weep holes 99 are also located on the protective sheath 80 with approximately 90 degrees of circumferential separation from the first pair of weep holes 99. The weep holes 99 are intended to prevent fluid from the surgical site coming into contact with the bearing 88, which may otherwise shorten the operational life of the bearing 88. During use, and owing to temperature gradients in the tool 20 and capillary effects, fluid may tend to move between the shaft 70 of the energy applicator 24 and the protective sheath 80 toward the bearing 88. The weep holes 99 provide a suitable escape for such fluid before it reaches the bearing 88.

Still referring to FIG. 10, the axial connector assembly 92 includes a bushing 118 disposed within the connector member 102 at a proximal end of the connector member 102. The bushing 118 is generally cylindrical in shape with an aperture 120 extending axially therethrough. In some embodiments, the bushing 118 is fixed axially to the support sleeve 96 and/or the connector member 102. Alternatively, the bushing 118 may be floating within the support sleeve 96.

The axial connector assembly 92 further includes a cam member 122. The cam member 122 can also be referred to as a wedge member. The cam member 122 includes a reduced diameter portion 124 disposed in the aperture 120 of the bushing 118 to rotate relative to the support sleeve 96. The cam member 122 rotates relative to the support sleeve 96. The cam member 122 includes a cavity 126 extending axially from the proximal end thereof. The cavity 126 includes a tapered or sloped surface 128 (also referred to as a cam surface or a wedge surface) extending axially and radially inward. In the embodiment shown, the sloped surface 128 is in the form of a conical surface. The sloped surface 128 is arranged at an acute angle $\alpha_2$ relative to the tool axis T. In some embodiments, the sloped surface 128 is at an acute angle $\alpha_2$ greater than zero degrees and less than 90 degrees. In other embodiments, the acute angle $\alpha_2$ is 5-60 degrees, 10-30 degrees, or 10-20 degrees, relative to the axis T. The acute angles $\alpha_1$ and $\alpha_2$ are sized so that at least one engagement member 138, described further below, becomes wedged between the sloped surfaces 77, 128 to hold the shaft 70 of the energy applicator 24, yet is readily releasable from the shaft 70. The difference in the acute angles $\alpha_1$ and $\alpha_2$ may be 4-12 degrees, 6-10 degrees, 7-9 degrees, or 8 degrees relative to the axis T.

The axial connector assembly 92 includes a locking sleeve 130 disposed within the support sleeve 96. The locking sleeve 130 extends axially. The locking sleeve 130 is generally cylindrical in shape. The locking sleeve 130 has a passage 132 extending axially therethrough to receive the shaft 70. The locking sleeve 130 also includes a plurality of openings 134 extending radially therethrough near a distal end thereof to receive the engagement members 138. The openings 134 are sized and shaped to allow the engagement members 138 to be exposed radially inwardly relative to the locking sleeve 130 to engage the sloped surface 79. The openings 134 are also sized and shaped to allow the engagement members 138 to be exposed radially outwardly relative to the locking sleeve 130 to engage the sloped surface 128. The openings 134 may be sized and shaped to prevent the engagement members 138 from passing completely through the openings 134 thereby retaining the engagement members 138. The locking sleeve 130 includes a flange 136 extending radially outwardly. In the embodiment shown, the locking sleeve 130 is integral, unitary, and one-piece, but could be separate parts in other embodiments.

The engagement members 138 couple the shaft 70 to the cam member 122. In one embodiment, a plurality of engagement members 138 are used with one engagement member 138 disposed in each opening 134 of the locking sleeve 130. Each of the engagement members 138 is generally spherical in shape. It should be appreciated that the axial connector assembly 92 may include any number of engagement members 138 and corresponding openings 134. In the embodiment shown, the engagement members 138 are ball bearings, such as those formed of stainless steel or other suitable materials.

The axial connector assembly 92 also includes a bushing 140 disposed about the locking sleeve 130 and within the support sleeve 96. The bushing 140 is generally cylindrical in shape with an aperture 142 extending axially therethrough to allow the locking sleeve 130 to extend therethrough. The bushing 140 is fixed relative to the support sleeve 96 in the embodiment shown. In other embodiments, the bushing 140 is free to float within the support sleeve 96 between the cam member 122 and the locking sleeve 130.

The axial connector assembly 92 further includes a ring member 144 disposed about the locking sleeve 130 between the bushing 140 and the flange 136. The ring member 144 is generally cylindrical in shape. The ring member 144 has one or more pockets 145 extending radially therein. In one embodiment, a pair of opposed pockets 145 extend radially therein.

The support structure 94 includes one or more slots 146 in the support sleeve 96. The slots 146 extend radially therethrough and are arranged helically about an axis of the support sleeve 96. In the embodiment shown, opposing slots 146 are formed helically in the support sleeve 96. The slots 146 in the embodiment shown are located only partially about the support sleeve 96. The support structure 94 also includes one or more engagement members 148 disposed in the slots 146 and pockets 145 of the ring member 144. One of the engagement members 148 is disposed in each of the slots 146 and pockets 145. In the embodiment shown, the engagement members 148 are ball bearings, such as those formed of stainless steel or other suitable materials. However, other configurations are contemplated.

With reference to FIGS. 11-15, a collet assembly 157 cooperates with the support structure 94 to move the axial connector assembly 92 between locked and unlocked states. The collet assembly 157 includes a lock collar 158 which is movable relative to the support structure 94. The lock collar 158 is elongated axially. The lock collar 158 is generally cylindrical in shape. The lock collar 158 is disposed about a portion of the support sleeve 96 of the support structure 94.

Figure 15:
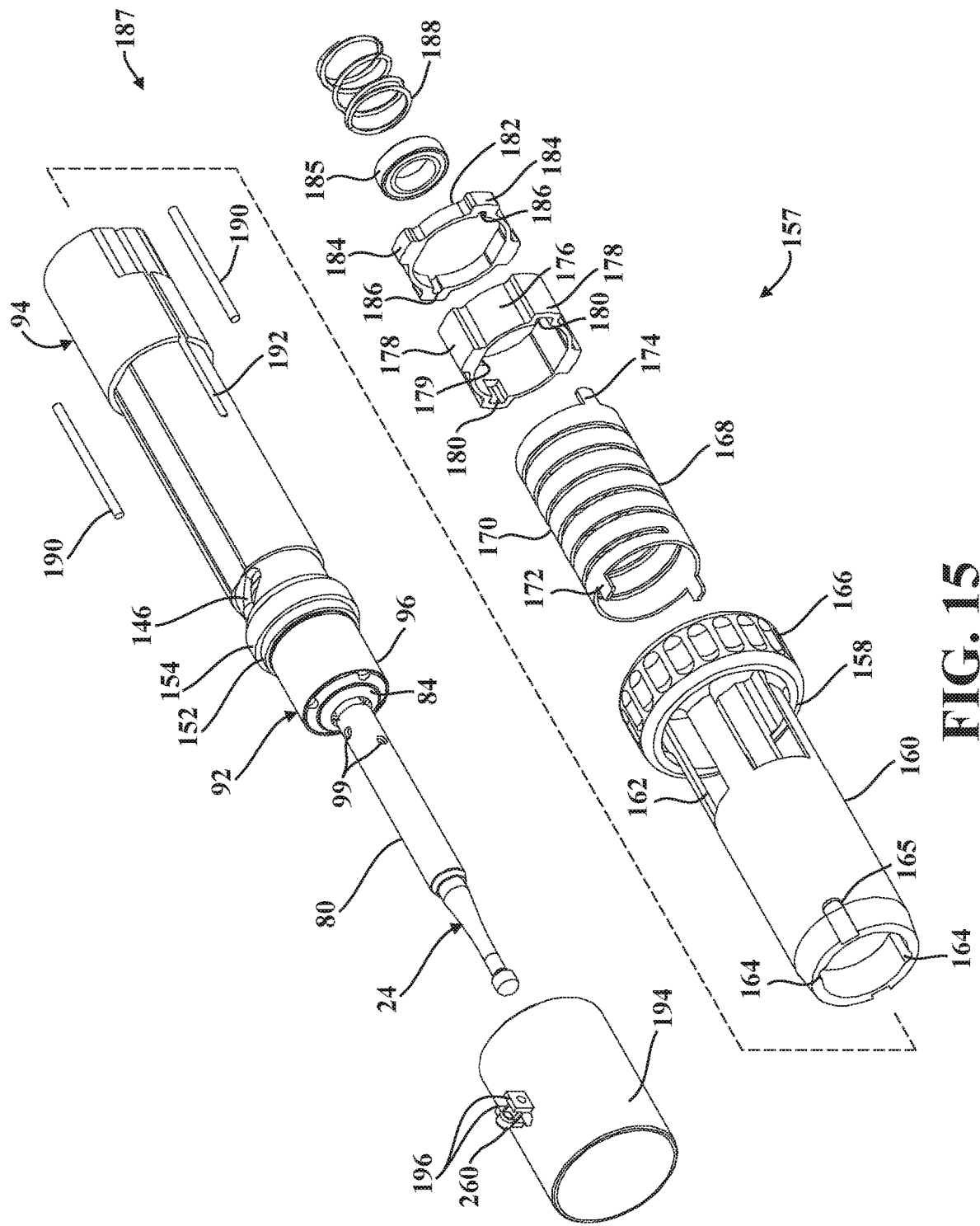
FIG. 15 is an exploded view of the collet assembly illustrating the energy applicator, protective sheath, the axial connector assembly, and the support structure being pre-assembled.

Referring to FIGS. 14 and 15, the lock collar 158 includes a wall 160 that defines cutouts 162 spaced circumferentially about the wall 160 and extending axially. The lock collar 158 includes one or more recesses 164 (see FIG. 15) extending axially inward from the distal end. The lock collar 158 also includes one or more pockets 165 (only one shown in FIG. 15) at a distal end extending axially inward. The collet assembly 157 also includes a release member coupled to the lock collar 158 which is configured to be actuated by the user to move the lock collar 158, such as to place the connector assembly 92 in the unlocked state. To this end, and in the embodiment illustrated in FIG. 15, the release member comprises a gripping member 166 at a proximal end of the lock collar 158 to be grasped by a user. The gripping member 166 is generally cylindrical in shape. It should be appreciated that the lock collar 158 may be rotated relative to the support sleeve 96 of the support structure 94.

The collet assembly 157 also includes a spring member 168 disposed within the lock collar 158. The spring member 168 extends axially. In the embodiment shown, the spring member 168 is a helical torsion spring. The spring member 168 is generally cylindrical in shape. The spring member 168 includes a plurality of convolutions 170. The spring member 168 includes at least one or more distal tabs 172 extending axially at a distal end. The distal tabs 172 are disposed inside the opposing pockets 165 of the lock collar 158 and are fixed to the lock collar 158. The spring member 168 includes at least one or more proximal tabs 174 extending axially at a proximal end.

The collet assembly 157 includes a first collar member 176 disposed over the support sleeve 96 of the support structure 94. The first collar member 176 is generally cylindrical in shape. The first collar member 176 includes a plurality of protrusions 178 extending axially and radially outward and a plurality of recesses 179 (one partially shown in FIG. 15) extending axially inward from a proximal end. The first collar member 176 also includes a recess 180 in two of the opposed protrusions 178 to receive the tabs 174 of the spring member 168.

The collet assembly 157 further includes a second collar member 182 disposed over the support sleeve 96 of the support structure 94. The second collar member 182 is generally cylindrical in shape. The second collar member 182 includes a plurality of protrusions 184 extending axially and radially outward. The second collar member 182 includes one or more recesses 186 extending axially through two of the opposed protrusions 184. The collet assembly 157 further includes a bushing 185 disposed against the flange 136 of the locking sleeve 130 to rotatably support the locking sleeve 130 in the support sleeve 96.

As illustrated, the axial connector assembly 92, support structure 94, and collet assembly 157 form a tool assembly 187. The tool assembly 187 includes a coil spring 188 disposed within the support sleeve 96 of the support structure 94. The coil spring 188 has a distal end that abuts the bushing 140. The tool assembly 187 includes a plurality of rods 190 disposed in grooves 192 extending axially along an outer periphery of the support sleeve 96 of the support structure 94. The rods 190 are also disposed in the recesses 179 of the first collar member 176 and the recesses 186 of the second collar member 182. It should be appreciated that the rods 190 key and rotatably fix the first collar member 176 and the second collar member 182 to the support sleeve 96.

In operation of the collet assembly 157, a user grasps the gripping member 166 and rotates the lock collar 158 clockwise (when viewed from the distal end) to allow disengagement of the energy applicator 24. As the lock collar 158 is rotated, the rods 190 rotationally lock the first collar member 176 and the second collar member 182 to the support sleeve 96. The lock collar 158 thus rotates against the bias of the spring member 168 (since the proximal end of the spring member 168 is prevented from rotating).

When rotating the lock collar 158, the engagement members 148 (e.g., ball bearings) are also moved in the slots 146 by virtue of the engagement members 148 being coupled to the lock collar 158, i.e., the engagement members 148 are positioned within the recesses 164 located in the distal end of the lock collar 158. Accordingly, movement of the engagement members 148 is controlled by rotation of the lock collar 158. Due to the helical nature of the slots 146, when moved by the lock collar 158, the engagement members 148 follow their corresponding helical paths such that the engagement members 148 are moved both in a planetary fashion about the tool axis T and axially with respect to the tool axis T toward the proximal end of the support sleeve 96. The lock collar 158 is configured to rotate, but not to translate relative to the axis T. As a result, the recesses 164 are axially elongated, so that as the lock collar 158 is rotated, and the engagement members 148 follow the helical paths in the slots 146, the engagement members 148 also translate within the recesses 164. In other embodiments, the lock collar 158 may also translate axially with the engagement members 148.

Axial movement of the ring member 144 is facilitated by the engagement members 148 being seated in the pockets 145 of the ring member 144 and captured between the pockets 145 and the recesses 164. In essence, the lock collar 158 is coupled to the ring member 144 through the engagement members 148. As a result, when the engagement members 148 are moved along their helical paths in the slots 146, the ring member 144 follows the engagement members 148 and is partially rotated and moved axially towards the flange 136. First, the ring member 144 reaches the flange 136 of the locking sleeve 130, and thereafter moves the locking sleeve 130 and associated bushing 185 proximally against the bias of spring 188. The engagement members 138 that were wedged between the sloped surfaces 77, 128 of the shaft 70 and the cam member 122 are thereby released from their wedged arrangement away from the sloped surface 77 defining the groove 76 of the shaft 70 to unlock the shaft 70 and allow removal of the energy applicator 24. This defines the unlocked state of the axial connector assembly 92. Since the slots 146 in the embodiment shown are only partially defined about the support sleeve 96, only partial rotation of the lock collar 158 is required to unlock the shaft 70 and allow removal of the energy applicator 24. The rotation required may be 180 degrees or less, 90 degrees or less, or 45 degrees or less.

When the gripping member 166 is released, the spring member 168 returns to its normal state thereby moving the engagement members 148 in the slots 146 in a reverse direction along their helical paths, which moves the ring member 144 distally to disengage the flange 136 of the locking sleeve 130, which allows the spring 188 to push the locking sleeve 130 back toward the cam member 122. The engagement members 138 fall back into the groove 76 against the sloped surface 77 of the shaft 70 of the energy applicator 24 and wedge against the sloped surface 128 to lock the shaft 70. This defines the locked state of the axial connector assembly 92. The collet assembly 157 operates the axial connector assembly 92 between the locked and unlocked states.

It should be appreciated that, when the energy applicator 24 is connected and locked to the tool assembly 187, the collet assembly 157 cooperates with the axial connector assembly 92 to apply a force to keep the proximal end 72 of the energy applicator 24 abutting against a shoulder 189 of the tool assembly 187. In particular, when the engagement members 138 are wedged between the sloped surfaces 77, 128, under the influence of the spring 188, these engagement members 138 impart a force directed against the sloped surface 77 of the energy applicator 24. This force includes an axial component applied against the energy applicator in the proximal direction to maintain the abutting contact between the proximal end 72 of the energy applicator 24 and the shoulder 189 (or other reference surface fixed relative to the support structure 94). Thus, the sloping surface 77 of the energy applicator 24 may also be referred to as an axial-force receiving surface.

One purpose of the abutment between the proximal end 72 and the shoulder 189 is to consistently match up and enable communication between an identification tag (e.g., a radio frequency identification tag RFID) on the energy applicator 24 and a radio frequency identification reader 199 (FIG. 19) on the tool assembly 187. This engagement of the proximal end 72 of the energy applicator and the shoulder 189 also provides repeatability in establishing the location (e.g., position in X, Y, Z coordinates) of a tool center point (TCP) of the energy applicator 24 for purposes of surgical navigation as described herein. For instance, the location of the TCP may be calibrated during manufacture and the details of the calibration, e.g., calibration data, thereafter stored in the RFID tag or other non-volatile memory for retrieval by a tool controller (not shown) that controls operation of the tool 20, the manipulator controller 60, and/or the navigation controller 62. By virtue of having a consistent interface (e.g., abutting contact) between the tool assembly 187 and the energy applicator 24, the system 10 (which includes the navigation system 32) is capable of retrieving the calibration data to readily determine the TCP in a coordinate system of the tool 20 or other coordinate system with high accuracy. Accordingly, the shoulder 189 provides a reference location from which to locate the TCP.

Referring to FIGS. 16-21, a drive assembly 200 of the tool 20 is shown. The drive assembly 200 includes a drive member 202, e.g., a rotating drive shaft. The drive member 202 is generally cylindrical in shape. The drive member 202 includes a cavity 204 (see FIG. 19) extending axially inwardly from a proximal end, a cavity 206 extending axially inwardly from a distal end, and a passage 208 extending axially between the cavities 204 and 206. The drive member 202 includes a seal 210 disposed in the cavity 204 and a seal 212 disposed in the cavity 206. The drive member 202 includes a flange 214 extending circumferentially and radially outward. The drive member 202 further includes a pair of opposed flanges 216 extending axially from a proximal end. In the embodiment shown, the drive member 202 is integral, unitary, and one-piece, but could be separate parts in other embodiments. It should be appreciated that the seal 210 seals against a rotatable shaft 252 of an actuator 250 (see FIG. 21) to be described and the seal 212 seals against the shaft 70 of the energy applicator 24. In the embodiment shown, the seal 212 may comprise a lip seal.

The drive assembly 200 also includes a driven member 218 coupled to the drive member 202. The driven member 218 extends axially. The driven member 218 is generally cylindrical in shape. The driven member 218 is disposed about the distal end of the drive member 202 and abuts the flange 214. In the embodiment shown, the driven member 218 is integral, unitary, and one-piece, but could be separate parts in other embodiments.

The drive assembly 200 includes a drive connector 220 coupled to the driven member 218 to rotate with the driven member 218. The drive connector 220 is generally cylindrical in shape. The drive connector 220 includes a cavity 222 extending axially inwardly from a proximal end and a cavity 224 extending axially inwardly from a distal end. The drive connector 220 includes a flange 226 extending circumferentially and radially outward that abuts the distal end of the driven member 218. In the embodiment shown, the drive connector 220 is integral, unitary, and one-piece, but could be separate parts in other embodiments.

The drive assembly 200 further includes a clutch assembly 228 disposed within the driven member 218 and configured to slideably receive the shaft 70 of the energy applicator 24. The clutch assembly 228 is supported by the driven member 218 and rotatable relative to the drive member 202. The clutch assembly 228 receives the shaft 70 of the energy applicator 24 for selectively coupling the shaft 70 to the drive member 202. Specifically, the shaft 70 is slideable into the clutch assembly 228 and is slideable out of the clutch assembly 228.

With reference to FIGS. 16-20, the clutch assembly 228 includes a plurality of roller holders 230 spaced axially and disposed within the driven member 218. Each of the roller holders 230 is generally cylindrical in shape. In the embodiment shown, each of the roller holders 230 are generally disc-shaped. Each of the roller holders 230 includes an interior aperture 232 extending axially therethrough. Each of the roller holders 230 also includes opposed flanges 234 extending radially inward. Each of the roller holders 230 includes a secondary aperture 236 extending axially through one of the flanges 234 and spaced from the interior aperture 232. Each of the roller holders 230 includes a recess 238 extending radially into the opposing flange 234. In the embodiment shown, each of the roller holders 230 is integral, unitary, and one-piece, but could be separate parts in other embodiments. In one embodiment, three roller holders 230 are disposed adjacent each other at a proximal end of the clutch assembly 228 and three roller holders 230 are disposed adjacent each other at a distal end. These two sets of roller holders 230 are spaced axially from one another and are collectively referred to as a cage. Each of the three roller holders 230 at each axial end are oriented so that their respective secondary apertures 236 and recesses 238 are arranged approximately 120 degrees circumferentially relative to each other.

The clutch assembly 228 also includes a plurality of rollers 240 coupled to the roller holders 230. The rollers 240 extend axially. The rollers 240 are generally cylindrical in shape. Each of the rollers 240 has a shaft 242 extending axially from each axial end. The two shafts 242 of a first roller 240 are disposed in the apertures 236 of the two outermost (axially) roller holders 230, the two shafts 242 of a second roller 240 are disposed in the apertures 236 of the two innermost (axially) roller holders 230, and the two shafts 242 of a third roller 240 are disposed in the apertures 236 of the remaining two roller holders 230. The rollers 240 are arranged to be generally parallel to the shaft 70 of the energy applicator 24 when the energy applicator 24 is coupled to the tool assembly 187.

The clutch assembly 228 also includes a plurality of counterweights 244 coupled to the roller holders 230. The counterweights 244 extend axially. The counterweights 244 are generally cylindrical in shape. One of the counterweights 244 is disposed in the recesses 238 of each pair of opposing roller holders 230, i.e., the two outermost roller holders 230, the two innermost roller holders 230, and the remaining two roller holders 230, so that there is one counterweight that corresponds to each roller 240. It should be appreciated that the roller holders 230, rollers 240, and counterweights 244 are radially movable relative to the shaft 70 of the energy applicator 24.

The clutch assembly 228 further includes a pair of resilient members 246 disposed about the rollers 240 and counterweights 244. The resilient members 246 are spaced axially from each other. The resilient members 246 are of an O-ring type. The resilient members 246 are made of a flexible material. The resilient members 246 act to press the rollers 240 against the shaft 70 during initial insertion of the shaft 70 into the clutch assembly 228. During insertion, the shaft 70 is located radially inward of the rollers 240. The resilient members 246 provide enough biasing force so that once the shaft 70 is initially inserted, the rollers 240 frictionally engage and hold the shaft 70 from falling out of the clutch assembly 228 due to gravity, i.e., before the axial connector assembly 92 is moved back to the locked state to permanently hold the energy applicator 24 in place.

Figure 20:
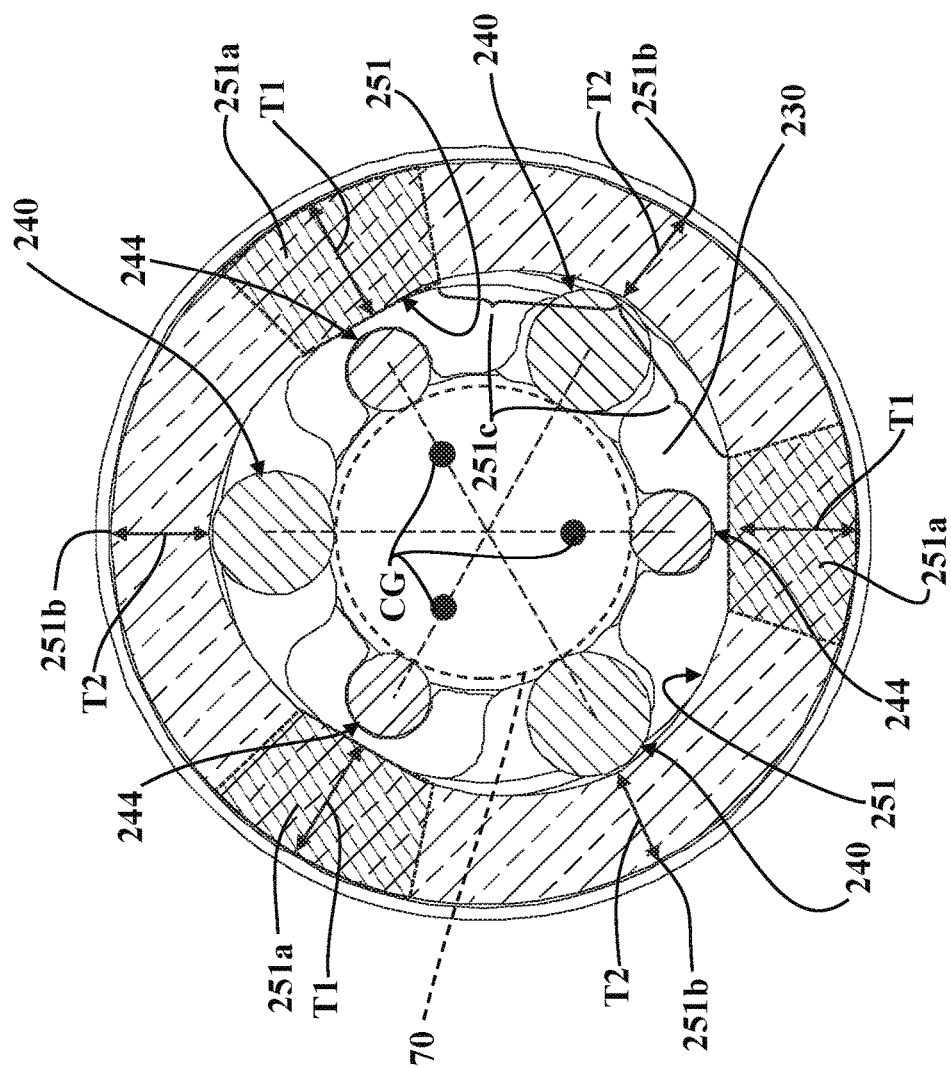
FIG. 20 is a cross-sectional view taken along line 20-20 of FIG. 18.

Referring to FIG. 20, in operation of the clutch assembly 228, when torque is applied and the driven member 218 is rotated, an inner cam surface 251 of the driven member 218 rotates until the inner cam surface 251 engages the rollers 240. More specifically, the driven member 218 has a cross-sectional profile as shown in FIG. 20 that comprises a first region 251a of thickness T1, a second region 251b of thickness T2, which is less than T1, and the inner cam surface 251 is arcuate in shape from the first region 251a to the second region 251b to form cam regions 251c on either side of the second region 251b (only one labeled in FIG. 20). The cam regions 251c, when rotated relative to the clutch assembly 228 (either direction) eventually engage the rollers 240 and hold the rollers 240 against the shaft 70. In the embodiment shown, the outer surface of the driven member 218 is cylindrical.

During operation of the tool 20, the counterweights 244 oppose any centrifugal forces that might otherwise act on the rollers 240 to pull the rollers 240 away from the shaft 70. In other words, by virtue of being heavier than the rollers 240, centrifugal forces acting on the counterweights 244 are larger than those acting on the rollers 240 thereby providing resultant forces that maintain contact of the rollers 240 with the shaft 70, even at full speed. Roller 240/counterweight 244 pairs are shown by dotted lines in FIG. 20 with their paired centers of gravity CG illustrated. Thus, the clutch assembly 228 is counterweighted to maintain contact of the rollers 240 with the shaft 70 when torque is applied to the driven member 218 by the actuator 250.

The counterweights 244 may be made of denser material than the rollers 240. In one embodiment, the counterweights 244 are formed of tungsten carbide and the rollers 240 are formed of stainless steel. So, even though the counterweights 244 may be smaller in volume, they are heavier so that the center of gravity CG of each roller 240/counterweight 244 pair is located closer to the counterweight 244. It should be appreciated that the clutch assembly 228 essentially floats inside the driven member 218 with enough space to accommodate some radial and/or axial movement of the roller holders 230, rollers 240, and counterweights 244. In the embodiment shown, the clutch assembly 228 comprises three clutch subassemblies, each subassembly comprising a pair of the roller holders 230 and one roller 240/counterweight 244 pair interconnecting the pair of the roller holders 230. The clutch subassemblies are able to shift relative to one another within the driven member 218.

Figure 16:
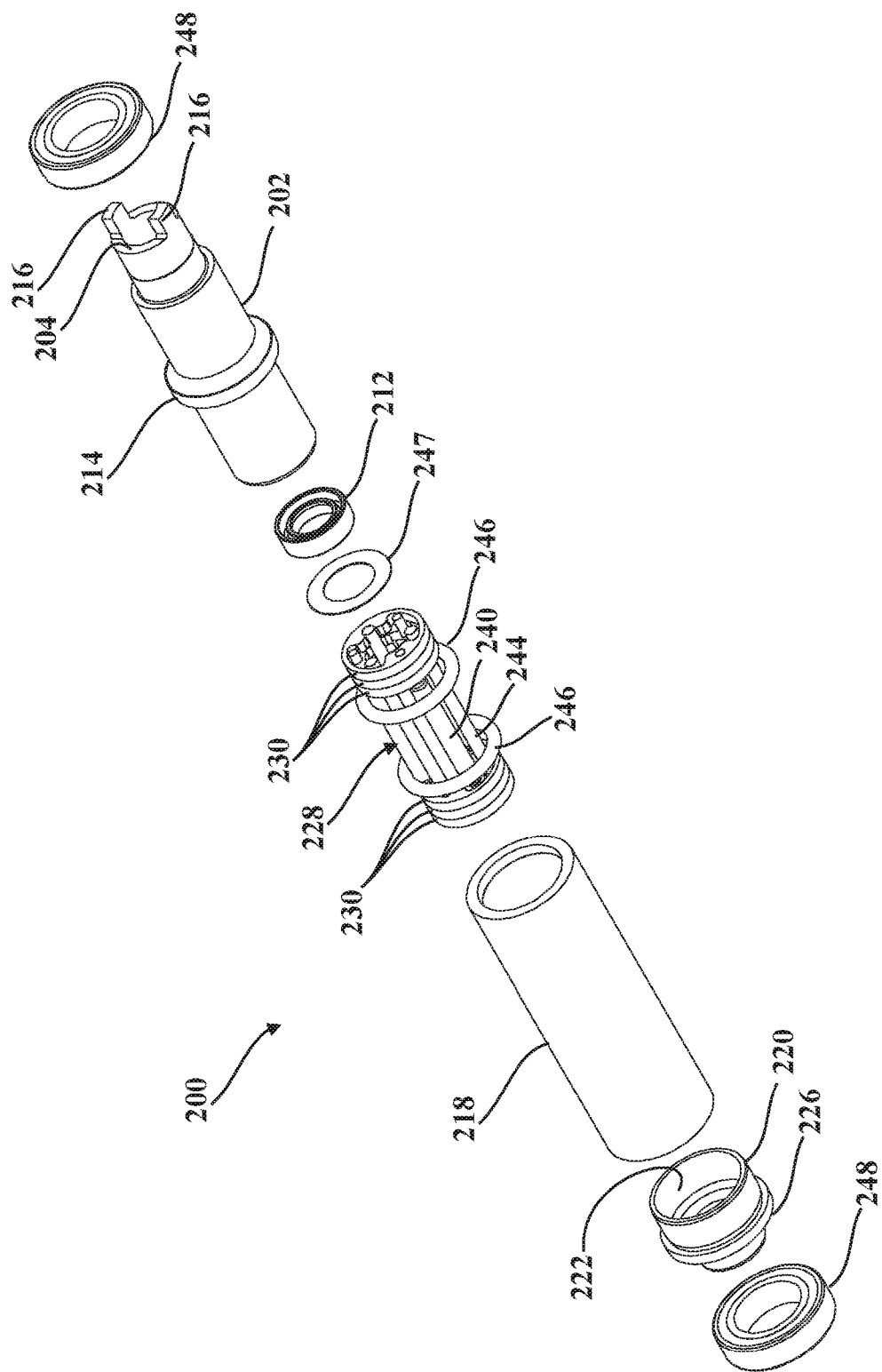
FIG. 16 is an exploded view of a drive assembly of the surgical tool.
Figure 17:
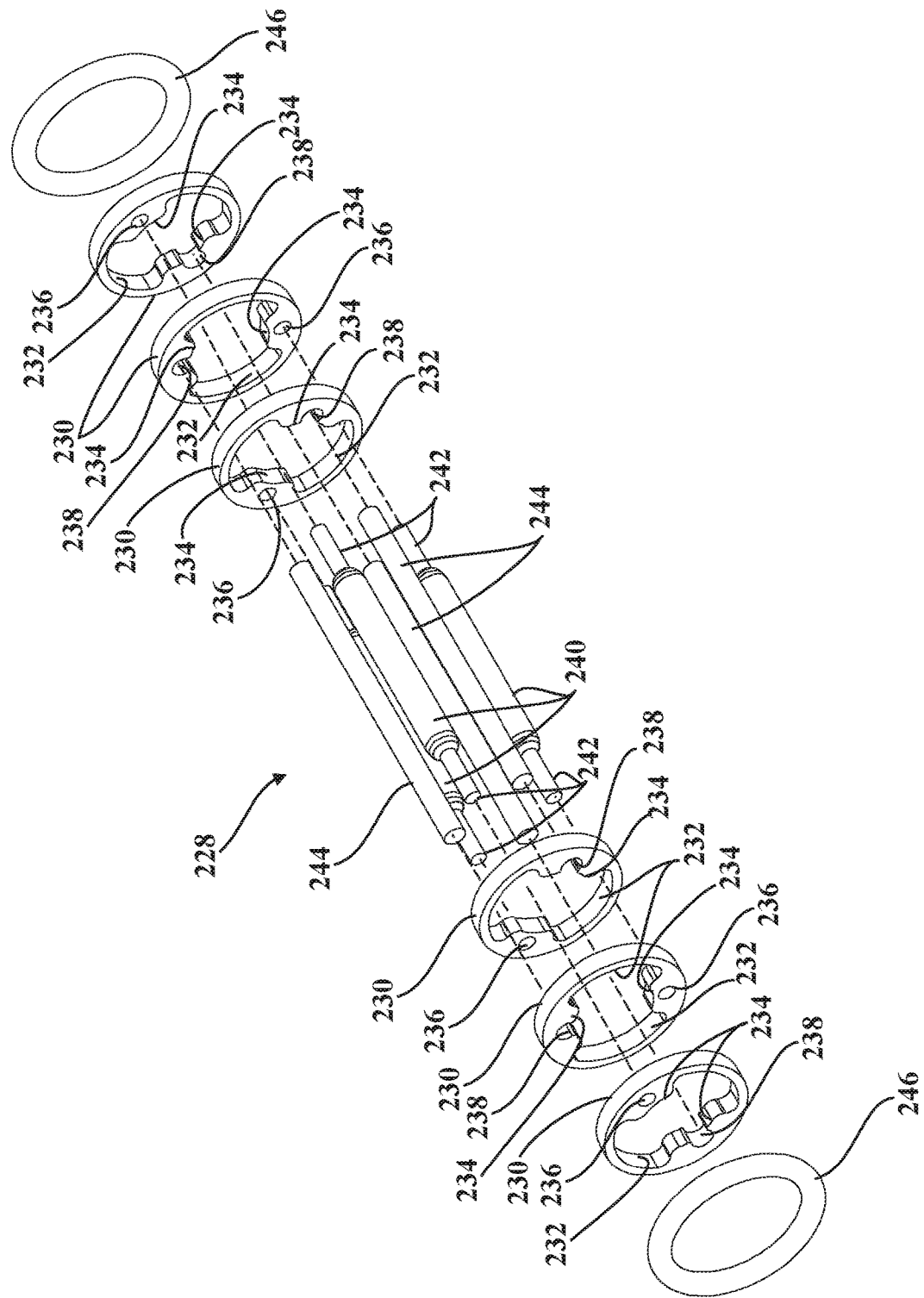
FIG. 17 is an exploded view of a clutch assembly of the drive assembly of FIG. 16.

Referring to FIGS. 16 and 19, the drive assembly 200 includes a washer 247 disposed between the seal 212 and the clutch assembly 228. The drive assembly 200 further includes bushings 248 disposed about the drive member 202 and the drive connector 220 to support the drive member 202, driven member 218, drive connector 220, and clutch assembly 228 for rotation within the support structure 94. Bearings may be used in place of one or more of the bushings 248 in some embodiments.

Figure 21:
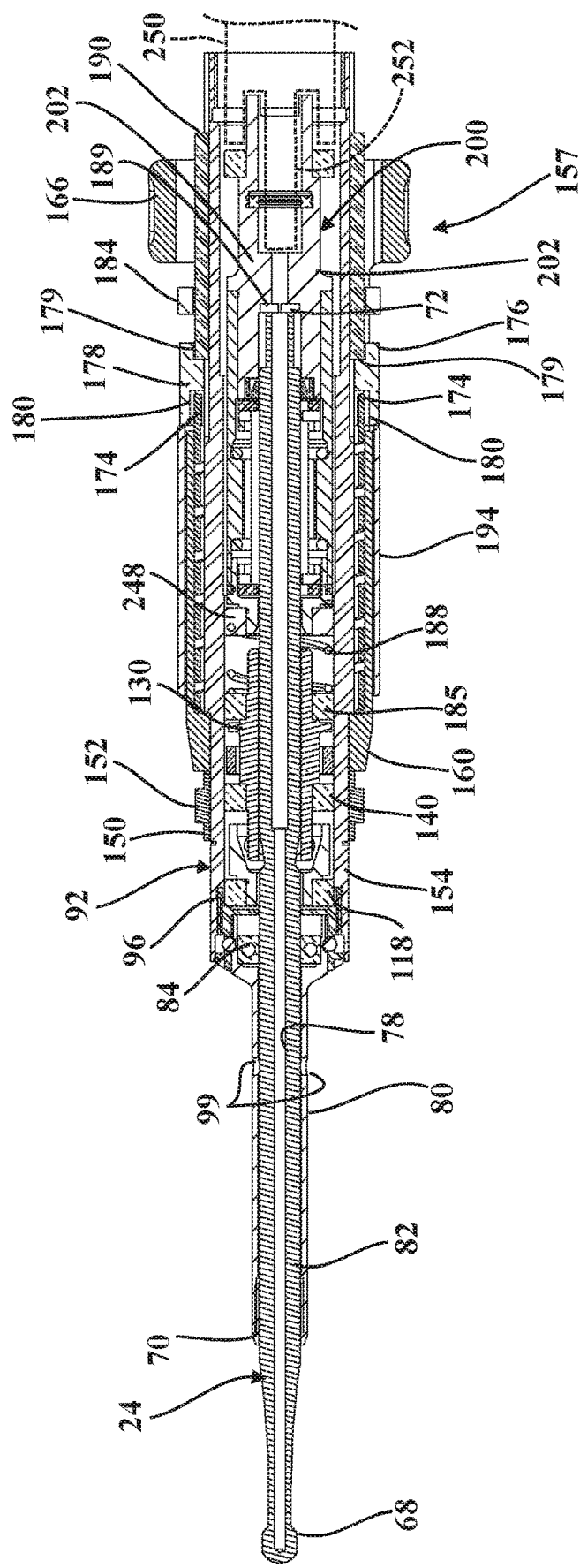
FIG. 21 is another cross-sectional view showing the energy applicator, protective sheath, axial connector assembly, support structure, collet assembly, and drive assembly.

Referring to FIG. 21, the actuator 250 is coupled to the drive assembly 200 to form a drive system. More specifically, the actuator 250 is coupled to the drive member 202 to impart rotation to the drive member 202. The actuator 250 is of a motor type and includes the shaft 252. The shaft 252 engages the drive member 202 and the opposed flanges 216 to rotate the drive member 202.

The support structure 94 further includes a floating collar or bushing 150 disposed about and movable relative to the support sleeve 96. The floating collar 150 is generally cylindrical in shape. The floating collar 150 includes a raised portion 152 extending radially outward. The support structure 94 includes a retaining ring 154 disposed in a groove 156 (see FIG. 10) in the support sleeve 96 to distally retain axial movement of the floating collar 150. It should be appreciated that the floating collar 150 may be movable axially along and rotatably about the support sleeve 96. In the embodiment shown, the floating collar 150 is rotatable about the support sleeve 96 and generally axially constrained between the retaining ring 154 and the lock collar 158.

The tool assembly 187 also includes an outer floating sheath 194 rotatably disposed about a portion of the lock collar 158. The floating sheath 194 is generally cylindrical in shape. The floating sheath 194 includes a pair of flanges 196 (see FIGS. 3 and 12) spaced from one another and extending outwardly in an equal and parallel manner from an outer surface of the floating sheath 194. Each of the flanges 196 includes an aperture 198 extending therethrough.

Referring to FIG. 3, a grip comprises a pair of grip members 258. The grip members 258 are sized and shaped to engage the floating collar 150 and the second collar member 182 in a clam-shell manner about the outer floating sheath 194 so that the grip is able to rotate relative to the support sleeve 96 during operation. A trigger 197 is pivotally connected to the grip members 258 near a proximal end of the grip members 258 by a suitable mechanism such as a pin. During actuation, the trigger 197 pivots relative to the grip members 258. The trigger 197 is also coupled to the outer floating sheath 194 by a link or lever 260 (see FIGS. 13 and 14). More specifically, the lever 260 is pivotally connected at one end to the flanges 196 of the outer floating sheath 194 by a suitable mechanism such as a pin. The other end of the lever 260 is pivotally connected to the trigger 197 at a location spaced from the pivot connection of the trigger 197 with the grip members 258.

In operation, when the trigger 197 is depressed (toward the tool axis T), the trigger 197 applies a force on the link 260, which in turn moves the link 260. The link 260 is arranged at an acute angle to the tool axis T (see FIG. 14) such that the link 260 applies an axially-directed force to the outer floating sheath 194 thereby moving the outer floating sheath 194 toward the actuator 250. Since the outer floating sheath 194 axially abuts the protrusions 178 of the first collar member 176, the first collar member 176 is also urged proximally. As previously described, the rods 190 are disposed in the recesses 179 of the first collar member 176 such that as the first collar member 176 moves proximally relative to the support sleeve 96, the rods 190 are also pushed proximally. Proximal ends of the rods 190 are seated in pockets 205 (see FIG. 3) in a switch actuator 207 such that proximal movement of the rods 190 causes the switch actuator 207 to also move proximally to activate a switch (not shown). A spring (not shown) acts against the switch actuator 207, rods 190, first collar member 176, link 260, and/or outer floating sheath 194 to return them to their pre-actuation position. Depression of the trigger 197 may be required to energize the actuator 150, to switch between different modes, to enable operation of the tool 20, or the like. Other functions of the trigger 197 are contemplated.

As noted above, another embodiment of the tool 20 is depicted in FIGS. 22-25C. As will be appreciated from the subsequent description below, this embodiment is substantially similar to the embodiment illustrated in FIGS. 1-21, and both embodiments share similar structure and components, as well as similar features, advantages, and operational use. Thus, common structure and components between the embodiments are provided with the same reference numerals in the drawings and in the description below. Moreover, for the purposes of clarity, consistency, and brevity, certain structure and components common between the embodiments are not reintroduced or re-described below.

Referring now to FIGS. 22-25C, the illustrated embodiment of the tool 20 similarly employs the tool assembly 187 to secure and drive the energy applicator 24, which likewise has the axial-force receiving surface 77 formed in the shaft 70. To this end, the tool assembly 187 similarly employs the support structure 94, the axial connector assembly 92, the drive system 66 and clutch assembly 228, the collet assembly 157, the reference surface 189, and the protective sheath assembly 87. Each of these components, structural features, and assemblies generally cooperate to facilitate operation of the tool 20 in the same way as described above in connection with the embodiment illustrated in FIGS. 1-21, but are arranged and configured differently as described below.

Figure 22:
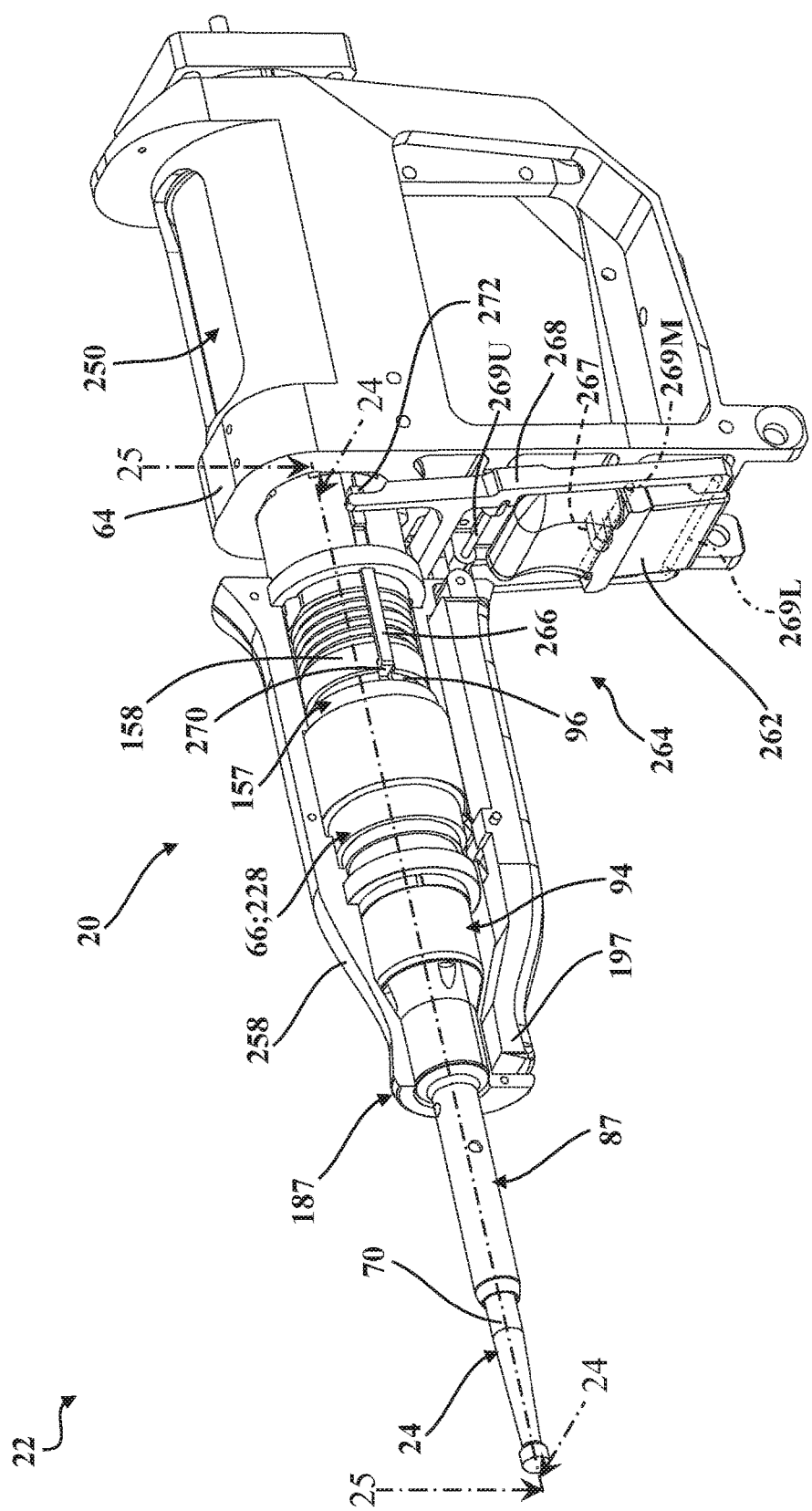
FIG. 22 is a partial perspective view of another embodiment of an end effector, a surgical tool, and an energy applicator, the surgical tool shown having a trigger arranged in a depressed position, and shown having a connector assembly arranged in a locked state.
Figure 23:
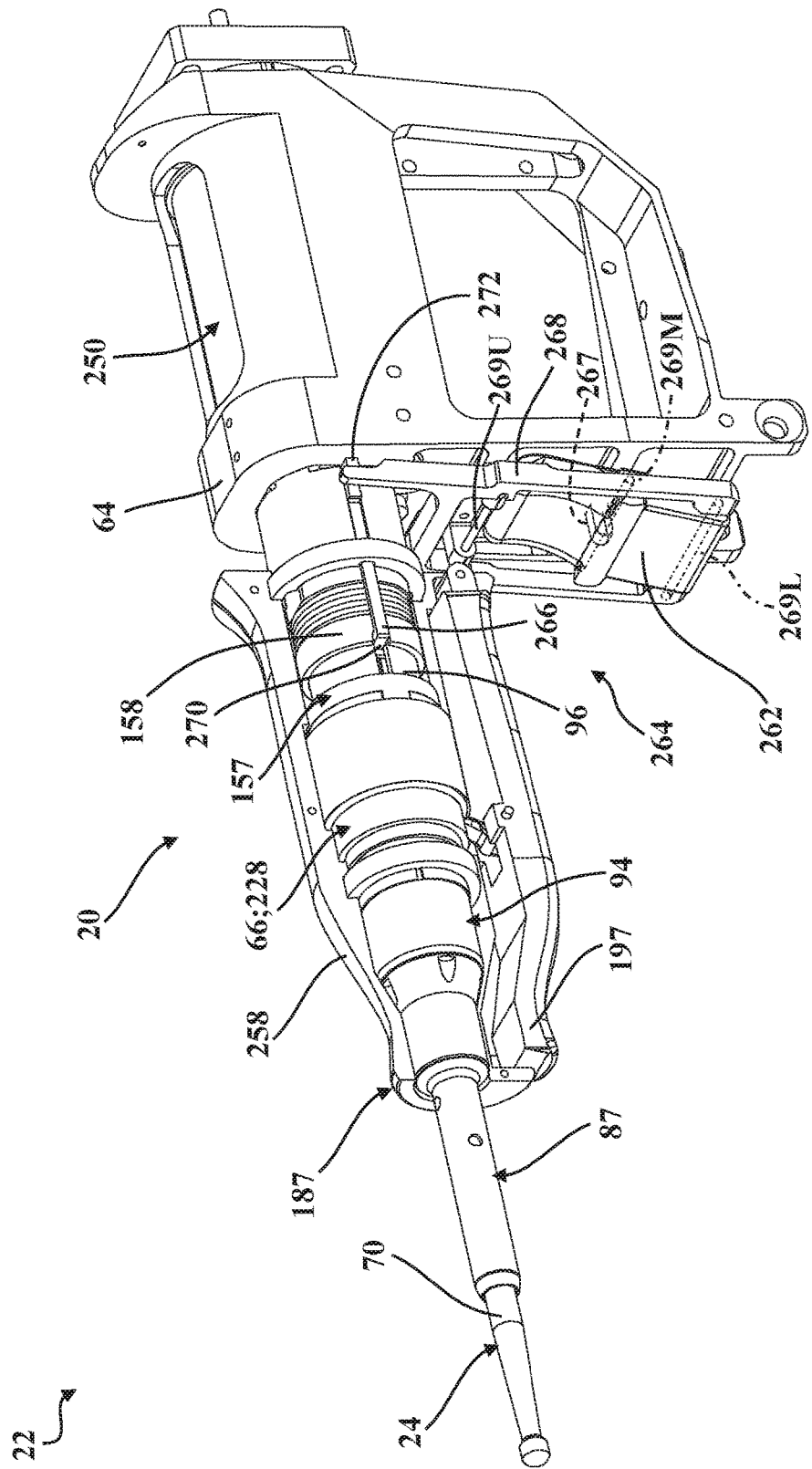
FIG. 23 is another partial perspective view of the end effector, surgical tool, and energy applicator of FIG. 22, shown with the trigger arranged in a released position, and shown with the connector assembly arranged in an unlocked state.
Figure 24A:
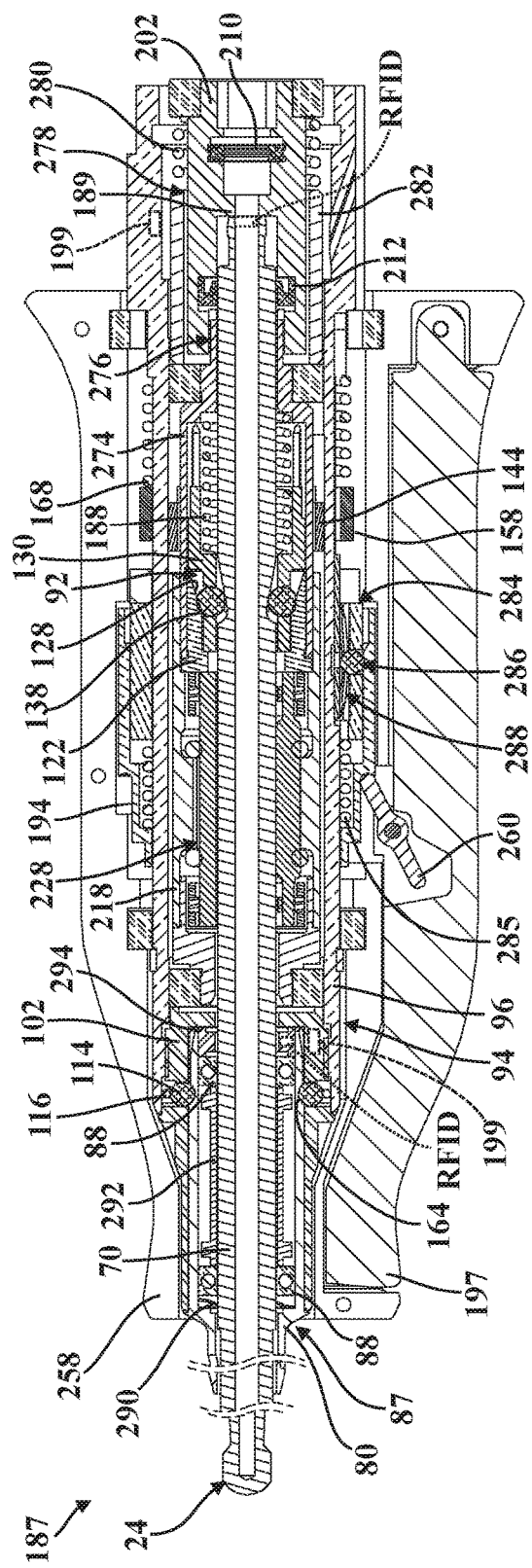
FIG. 24A is a broken sectional view of a portion of the surgical tool and energy applicator taken along line 24-24 in FIG. 22, shown with the trigger arranged in the depressed position, and shown with the connector assembly arranged in the locked state.
Figure 25A:
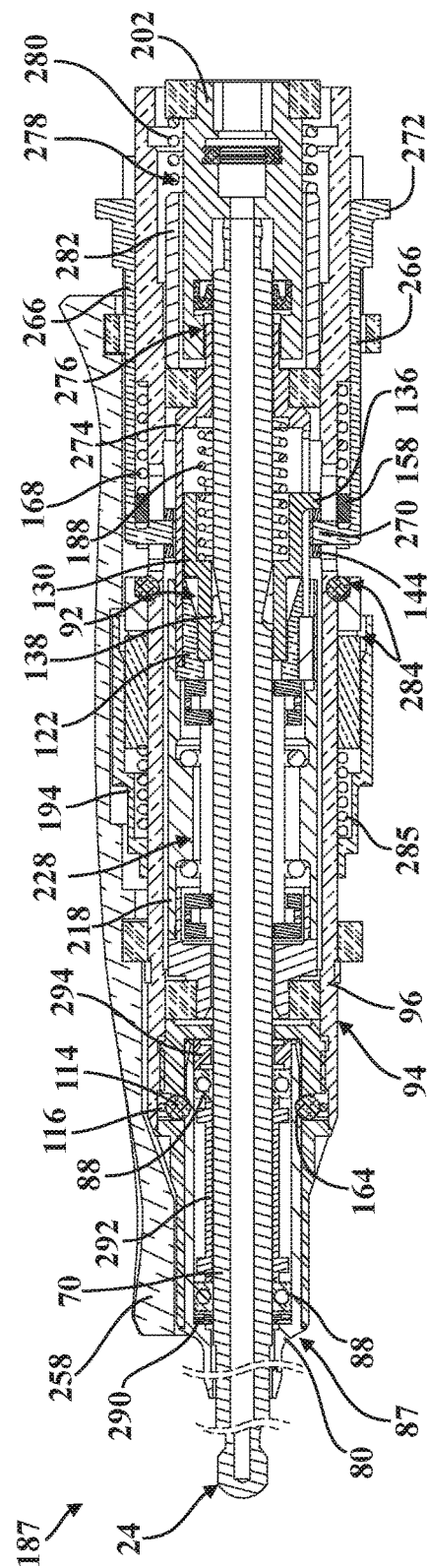
FIG. 25A is a broken sectional view of a portion of the surgical tool and energy applicator taken along line 25-25 in FIG. 22, shown with the trigger arranged in the depressed position, and shown with the connector assembly arranged in the locked state.
Figure 24B:
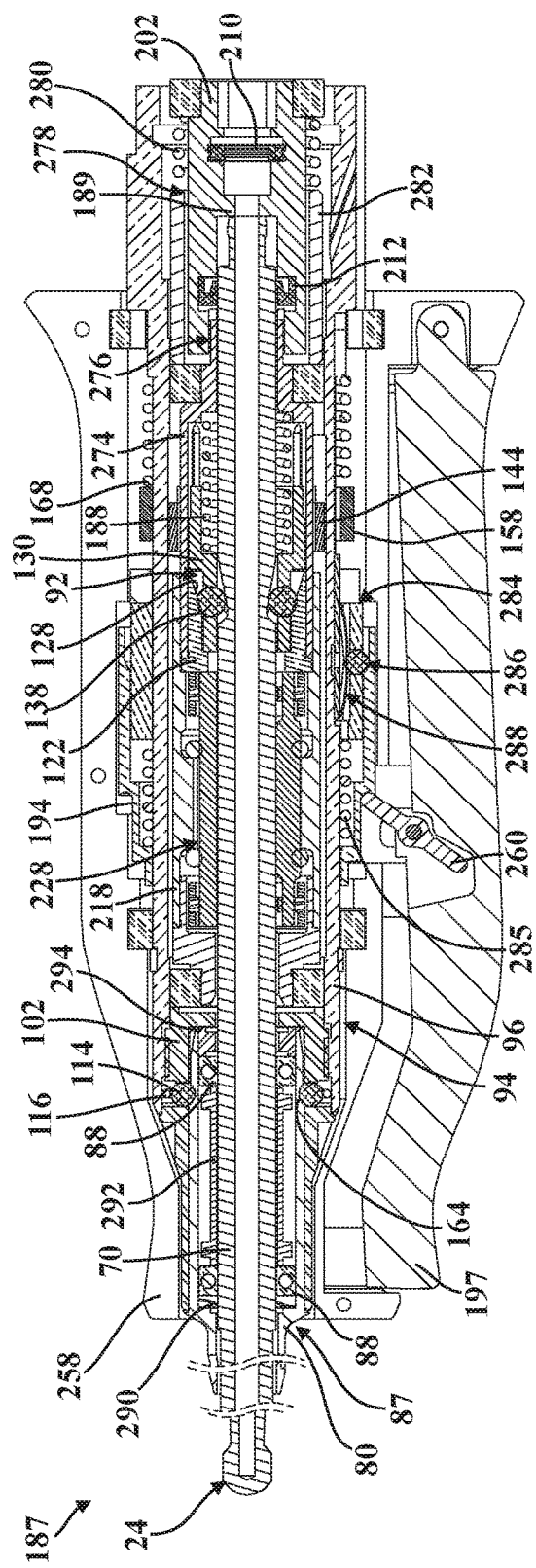
FIG. 24B is another partial broken sectional view of the surgical tool and energy applicator of FIG. 24A, shown with the trigger arranged in a released position, and shown with the connector assembly arranged in the locked state.
Figure 25B:
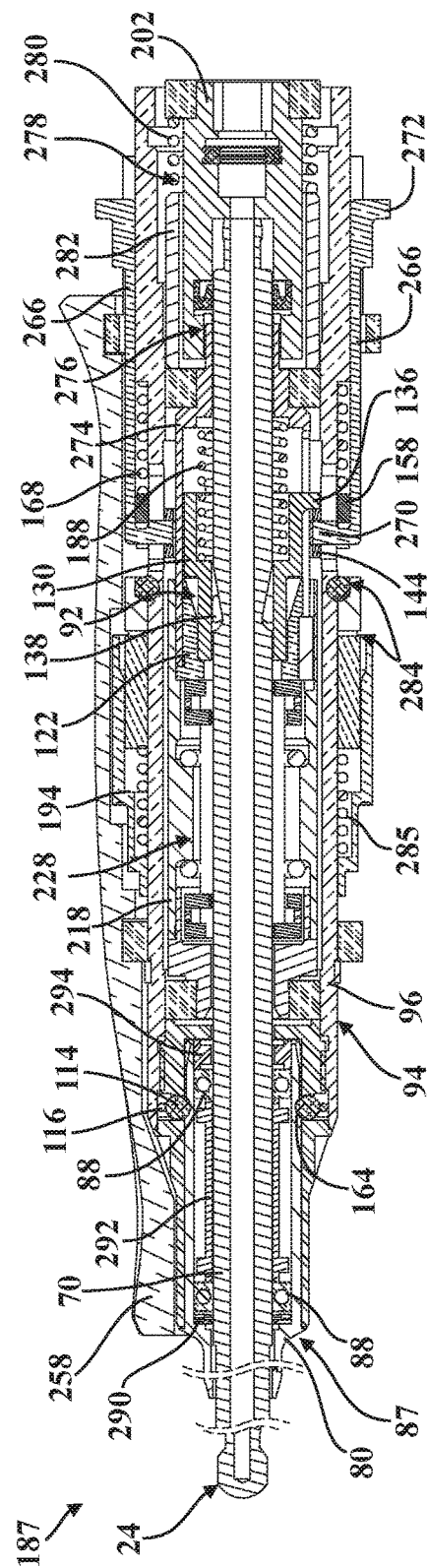
FIG. 25B is another partial broken sectional view of the surgical tool and energy applicator of FIG. 25A, shown with the trigger arranged in a released position, and shown with the connector assembly arranged in the locked state.
Figure 24C:
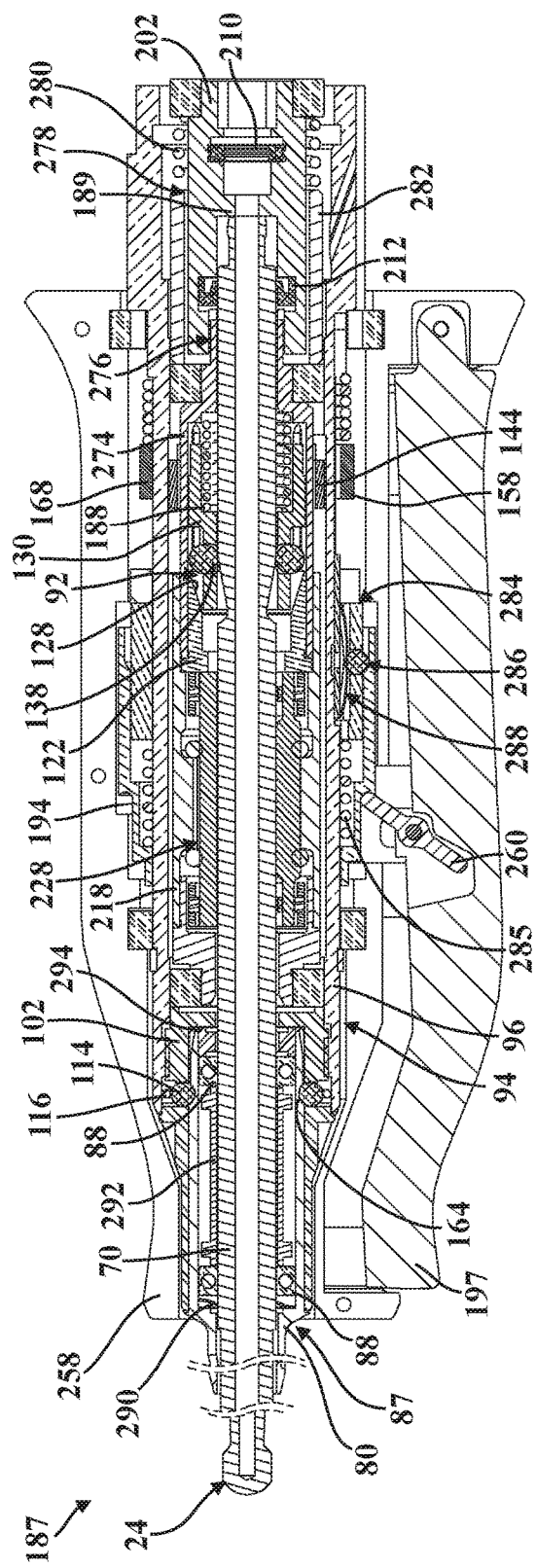
FIG. 24C is another partial broken sectional view of the surgical tool and energy applicator of FIGS. 24A-24B, shown with the trigger arranged in the released position, and shown with the connector assembly arranged in an unlocked state.
Figure 25C:
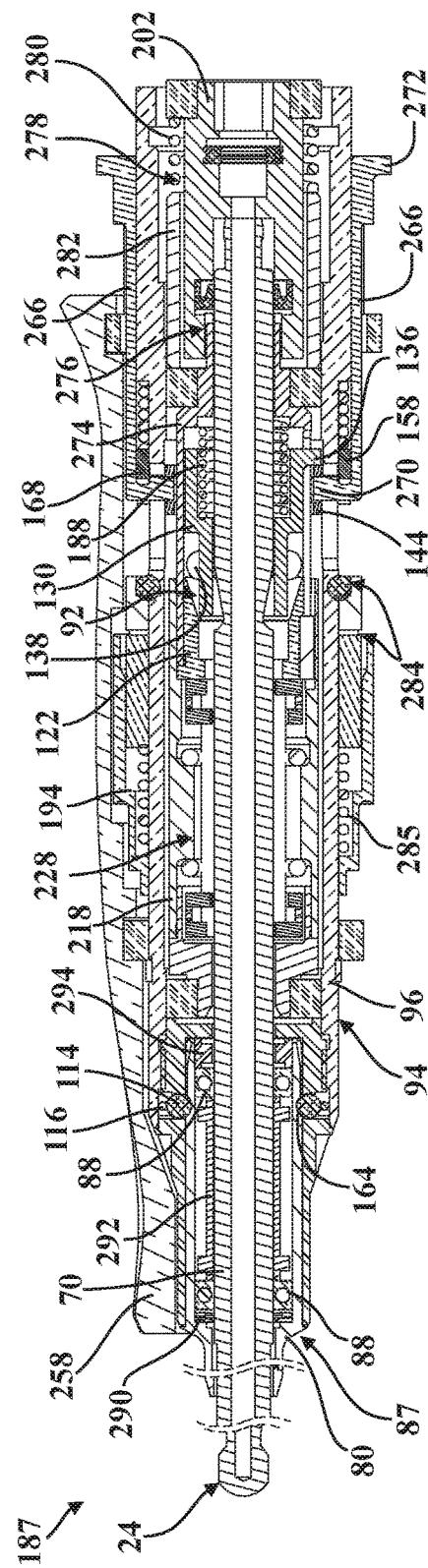
FIG. 25C is another partial broken sectional view of the surgical tool and energy applicator of FIGS. 25A-25B, shown with the trigger arranged in the released position, and shown with the connector assembly arranged in an unlocked state.

As shown in FIGS. 22-23, the illustrated tool assembly 187 likewise employs the release member and the lock collar 158 of the collet assembly 157 to facilitate movement of the axial connector assembly 92 between the locked state (see FIGS. 22, 24A, and 25A) and the unlocked state (see FIGS. 23, 24C, and 25C). However, in this embodiment, the lock collar 158 is slidably movable relative to the support structure 94. In order to facilitate sliding movement of the lock collar 158, the release member is realized in this embodiment as a release lever 262 which is coupled to the mounting fixture 64. Here, a release mechanism, generally indicated at 264, is interposed in force-translating relationship between the release lever 262 and the lock collar 158.

The release mechanism 264 comprises a pair of arms 266, an intermediate link 268, and pins which cooperate to facilitate pivoting movement of the release lever 262 and the intermediate link 268 relative to the mounting fixture 64. More specifically, an upper pin 269U, a lower pin 269L, and a middle pin 269M are provided in the illustrated embodiment. The upper pin 269U is coupled to the mounting fixture 64 and supports the intermediate link 268 for pivoting relative to the mounting fixture 64. The lower pin 269L (shown in phantom in FIGS. 22 and 23) is coupled to the release lever 262 and supports the intermediate link 268 for pivoting relative to the release lever 262. The middle pin 269M (shown in phantom in FIGS. 22 and 23) is coupled to the release lever 262 and is pivotally coupled to a portion 267 (shown in phantom in FIGS. 22 and 23) of the mounting fixture 64. Each of the arms 266 has a first tab 270 which engages the lock collar 158, and a second tab 272 which abuts the intermediate link 268. As shown in FIGS. 22-23, the arms 266 translate in a direction substantially parallel to the tool axis T in response to pivoting movement of the intermediate link 268 resulting from corresponding movement of the release lever 262. It will be appreciated that the release mechanism 264 could be arranged for actuation by the user in a number of different ways.

As shown in FIGS. 25A and 25C, the lock collar 158 is biased axially via the spring member 168 which, in this embodiment, is realized as a cylindrical compression spring interposed between the support sleeve 96 and the lock collar 158 (see FIGS. 25A and 25C). As a result of the force exerted on the lock collar 158 from the spring member 168, the axial connector assembly 92 is biased toward the locked state. In addition to engaging and moving the lock collar 158, the arms 266 also engage and facilitate movement of the ring member 144 which, in turn, abuts the flanges 136 of the locking sleeve 130. Here, the locking sleeve 130 is biased by the spring 188 and similarly moves axially to bring the engagement members 138 into abutment between the axial-force receiving surface 77 of the energy applicator 24 and the tapered or sloped surface 128 of the cam member 122 (see FIG. 24A).

As shown in FIGS. 24A-25C, in the illustrated embodiment, the driven member 218 is coupled to a drive sleeve 274 which, in turn, is coupled to the cam member 122 such that the driven member 218, the drive sleeve 274, and the cam member 122 move concurrently. The drive sleeve 274 rotates with the drive member 202 via a coupling arrangement, generally indicated at 276, which may comprise a keyed, splined, or similar arrangement of structural features which cooperate to engage and facilitate concurrent rotation. Adjacent to the coupling arrangement 276, a preload assembly 278 with a preload spring 280 and a collar member 282 are provided. It will be appreciated that the driven member 218 could be coupled to the drive member 202 in a number of different ways.

Referring again to FIGS. 22-25C, in the illustrated embodiment, the trigger 197 is similarly arranged for actuation by the user. Here too, movement of the trigger 197 causes corresponding movement of the link or lever 260, which abuts and translates force to the outer floating sheath 194. Here in this embodiment, the outer floating sheath 194 is disposed about the support sleeve 96 and translates axially in response to force acting on the trigger 197, and a trigger return mechanism 284 with a return spring 285 facilitates limited, biased, axial movement of the outer floating sheath 194 relative to the support sleeve 96. As shown in FIGS. 24A-24B, the outer floating sheath 194 is shaped such that movement of the trigger 197 causes corresponding movement of a trigger actuator 286 (e.g., a ball bearing) supported by a portion of the trigger return mechanism 284. Here, movement of the trigger actuator 286 causes corresponding movement of a switch mechanism 288 (e.g., a piezoelectric switch) configured to facilitate operation of the tool assembly 187, such as by generating a variable signal used to effect corresponding variable rotation of the actuator 250. However, it will be appreciated that the trigger 197 could be configured in a number of different ways sufficient to facilitate operation of the tool assembly 187.

As noted above, the embodiment illustrated in FIGS. 22-25C also employs a removably-attachable protective sheath assembly 87. Here too in this embodiment, the resilient member 116 biases one or more engagement members 114 toward the tool axis T and into engagement with the recesses 164 formed in the protective sheath 80. It will be appreciated that any suitable number of engagement members 114 could be employed to engage in any suitable number of recesses 164. In this embodiment, the protective sheath assembly 87 comprises a pair of bearings 88 supported in the protective sheath bore 82, a bearing biasing element 290, a spacer 292, and an end cap 294. Here, the spacer 292 is disposed between the bearings 88. The bearing biasing element 290 biases the bearings 88 and the spacer 292 proximally toward the end cap 294. The end cap 294 retains the bearings 88, the spacer 292, and the bearing biasing element 290 within the protective sheath bore 82.

As shown in FIG. 24A, in this embodiment, a tag (e.g., a radio frequency identification tag RFID) is coupled to the end cap 294, and a reader 199 is coupled to the connector member 120. Here, data (e.g., calibration data, usage data, and the like) that is stored on the tag RFID may be read by the reader 199 to, among other things, ensure that the proper protective sheath assembly 87 is being utilized for the surgical procedure, determine the expected life of and/or determine replacement or service of the protective sheath assembly 87 after a predetermined amount of use, and the like. Data may also be written onto the tag RFID via the reader 199, such as to update the tag RFID after a surgical procedure with a new expected life, number of cycles, duration of use, and the like. Here too as shown in FIG. 24A, other tags RFID and/or readers 199 may be employed to, among other things, identify the specific energy applicator 24 being utilized via calibration data. Other configurations are contemplated.

The embodiments of the systems 10 and tools 20 described herein afford significant advantages in connection with a broad number of medical and/or surgical procedures including, for example, where surgical manipulators 14 are employed. Specifically, it will be appreciated that the embodiments of the tool assembly 187 described and illustrated herein are configured such that the energy applicator 24 can be releasably attached in a simple, efficient, and reliable manner, and can be driven to manipulate patient 12 tissue in a number of different ways to accommodate different surgical procedures, user preference, and the like.

The present invention has been described in an illustrative manner. It is to be understood that the terminology, which has been used, is intended to be in the nature of words of description rather than of limitation. Many modifications and variations of the present invention are possible in light of the above teachings. Therefore, the present invention may be practiced other than as specifically described.

The invention claimed is:

1. A tool comprising:
an energy applicator including a shaft extending along an axis between a proximal end and a distal end; and
a tool assembly comprising a support structure to support the energy applicator, a connector assembly arranged to engage and releasably lock the energy applicator to the support structure in a locked state, and a drive system coupled to the support structure and configured to rotatably drive the shaft of the energy applicator about the axis;
wherein the drive system comprises a counterweighted clutch assembly.

2. The tool as set forth in claim 1, wherein the clutch assembly includes a plurality of roller holders, a plurality of rollers, and a plurality of counterweights.

3. The tool as set forth in claim 2, wherein the clutch assembly comprises a plurality of clutch subassemblies, each of the clutch subassemblies comprising a pair of the roller holders, one of the rollers, and one of the counterweights.

4. The tool as set forth in claim 3, wherein each of the clutch subassemblies has a center of gravity located closer to the one of the counterweights than to the one of the rollers.

5. The tool as set forth in claim 3, wherein each of the plurality of clutch subassemblies are movable relative to the axis, and the plurality of counterweights and the plurality of rollers are weighted such that centrifugal forces acting on the clutch subassemblies urge the plurality of rollers into contact with the shaft of the energy applicator.

6. The tool as set forth in claim 2, wherein each of the counterweights are heavier than each of the rollers.

7. The tool as set forth in claim 2, wherein each of the counterweights are formed of a first material and each of the rollers are formed of a second material less dense than the first material.

8. The tool as set forth in claim 7, wherein the first material is tungsten carbide and the second material is stainless steel.

9. The tool as set forth in claim 2, wherein the drive system comprises a drive member and a driven member, the driven member having an inner cam surface shaped to selectively engage the plurality of rollers and radially press the rollers into contact with the shaft of the energy applicator upon rotation of the driven member.

10. A tool assembly for use with an energy applicator having a shaft extending along an axis between a proximal end and a distal end, the tool assembly comprising:
a support structure to support the energy applicator;
a connector assembly arranged to engage and releasably lock the energy applicator to the support structure in a locked state; and
a drive system coupled to the support structure and configured to rotatably drive the shaft of the energy applicator about the axis;
wherein the drive system comprises a counterweighted clutch assembly.

11. The tool assembly as set forth in claim 10, wherein the clutch assembly includes a plurality of roller holders, a plurality of rollers, and a plurality of counterweights.

12. The tool assembly as set forth in claim 11, wherein the clutch assembly comprises a plurality of clutch subassemblies, each of the clutch subassemblies comprising a pair of the roller holders, one of the rollers, and one of the counterweights.

13. The tool assembly as set forth in claim 12, wherein each of the clutch subassemblies has a center of gravity located closer to the one of the counterweights than to the one of the rollers.

14. The tool assembly as set forth in claim 12, wherein each of the plurality of clutch subassemblies are movable relative to the axis; and
wherein the plurality of counterweights and the plurality of rollers are weighted such that centrifugal forces acting on the clutch subassemblies urge the plurality of rollers into contact with the shaft of the energy applicator when the connector assembly engages and releasably locks the energy applicator to the support structure in the locked state.

15. The tool assembly as set forth in claim 11, wherein each of the counterweights are heavier than each of the rollers.

16. The tool assembly as set forth in claim 11, wherein each of the counterweights are formed of a first material and each of the rollers are formed of a second material less dense than the first material.

17. The tool assembly as set forth in claim 16, wherein the first material is tungsten carbide and the second material is stainless steel.

18. The tool assembly as set forth in claim 11, wherein the drive system comprises a drive member and a driven member, the driven member having an inner cam surface shaped to selectively engage the plurality of rollers and radially press the rollers into contact with the shaft of the energy applicator upon rotation of the driven member when the connector assembly engages and releasably locks the energy applicator to the support structure in the locked state.

* * * * *